US010704095B2

(12) United States Patent
Shiina et al.

(10) Patent No.: US 10,704,095 B2
(45) Date of Patent: Jul. 7, 2020

(54) METHOD AND KIT FOR DNA TYPING OF HLA GENE

(71) Applicant: GENODIVE PHARMA INC., Kanagawa (JP)

(72) Inventors: Takashi Shiina, Kanagawa (JP); Shingo Suzuki, Kanagawa (JP); Yuki Wada, Kanagawa (JP); Shigeki Mitsunaga, Kanagawa (JP); Hidetoshi Inoko, Kanagawa (JP)

(73) Assignee: GENODIVE PHARMA INC., Kanagawa (JP)

( * ) Notice: Subject to any disclaimer, the term of this patent is extended or adjusted under 35 U.S.C. 154(b) by 540 days.

(21) Appl. No.: 15/088,727

(22) Filed: Apr. 1, 2016

(65) Prior Publication Data

US 2016/0208326 A1 Jul. 21, 2016

Related U.S. Application Data

(62) Division of application No. 14/233,909, filed as application No. PCT/JP2012/062743 on May 18, 2012, now abandoned.

(30) Foreign Application Priority Data

Jul. 21, 2011 (JP) ................................. 2011-159832

(51) Int. Cl.
*C12Q 1/68* (2018.01)
*C12Q 1/6881* (2018.01)
*C12Q 1/6888* (2018.01)

(52) U.S. Cl.
CPC ......... *C12Q 1/6881* (2013.01); *C12Q 1/6888* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

2010/0086914 A1* 4/2010 Bentley ................ C12Q 1/6881
435/6.12

FOREIGN PATENT DOCUMENTS

| CN | 101962676 A | * | 2/2011 | ............... C12Q 1/68 |
|---|---|---|---|---|
| CN | 101962676 A | | 2/2011 | |
| EP | 0892069 A2 | | 1/1999 | |
| JP | H11-216000 A | | 8/1999 | |
| JP | 2011-500041 A | | 1/2011 | |
| WO | 2000061795 A2 | | 10/2000 | |
| WO | 2005042764 A2 | | 5/2005 | |
| WO | 2009049889 A1 | | 4/2009 | |
| WO | 2013011734 A1 | | 2/2015 | |

OTHER PUBLICATIONS

Bentley G, Higuchi R, Hoglund B, Goodridge D, Sayer D, Trachtenberg EA, Erlich HA. High-resolution, high-throughput HLA genotyping by next-generation sequencing. Tissue Antigens. Nov. 2009; 74(5):393-403 (Year: 2009).*
Hoglund, B., Holcomb, C.L., Moonsamy, P.V., Goodridge, D. and Erlich, H.A. Single pass very high resolution Hla genotyping by next generation sequencing with the 454 Life Sciences GS FLX and GS Junior. May 2011. Tissue Antigens, Abstracts. 77(5), p. 465 (Year: 2011).*
Lind C et al. Next-generation sequencing: the solution for high-resolution, unambiguous human leukocyte antigen typing. Hum Immunol. Oct. 2010; 71(10):1033-42. Epub Aug 5. 2010 (Year: 2010).*
Seurynck, K., and L. A. BaxterLowe. Use of 3' and 5' untranslated region polymorphism of class I HLA-B to determine full length nucleotide sequences. Human Immunology, Abstracts, 1997, vol. 55, pp. 28 (Year: 1997).*
Zhu F, He Y, Zhang W, He J, He J, Xu X, Lv H, Yan L. Analysis for complete genomic sequence of HLA-B and HLA-C alleles in the Chinese Han population. Int J Immunogenet. Aug, 2011; 38(4):281-4. Epub May 17, 2011. (Year: 2011).*
Kotsch et al. Sequencing of HLA class II genes based on the conserved diversity of the non-coding regions: sequencing based typing of HLA-DRB genes. Tissue Antigens. May 1999; 53(5):486-97. (Year: 1999).*
CN101962676—English Translation (Feb. 2, 2011, pp. 1-52). (Year: 2011).*
Holcomb et al. A multi-site study using high-resolution HLA genotyping by next generation sequencing. Tissue Antigens. Mar. 2011; 77(3):206-17. (Year: 2011).*
Zhu F, He Y, Zhang W, He J, He J, Xu X, Yan L. Analysis of the complete genomic sequence of HLA-A alleles in the Chinese Han population. International journal of immunogenetics. Dec. 2009; 36(6):351-60. (Year: 2009).*
Genbank Accession No. AY663400—*Homo sapiens* voucher Coriell Cell Repository DNA sample NA01018 MHC class II antigen (HLA-DQB1) gene, HLA-DQB1-DQB1 050101 allele, MHC class II antigen (HLA-DQA1) gene, HLA-DQA1-DQA1 010102 allele, and MHC class II antigen (HLA-DRB1) gene, complete cds (Sep. 2005) (Year: 2005).*

(Continued)

*Primary Examiner* — Gary Benzion
*Assistant Examiner* — Olayinka A Oyeyemi
(74) *Attorney, Agent, or Firm* — Pearne & Gordon LLP

(57) ABSTRACT

The purpose of the present invention is to provide a method and kit for highly precise DNA typing, in which ambiguity derived from phase ambiguity is eliminated. The present invention provides a method for the DNA typing of HLA, which is characterized by comprising: (1) a step of preparing a set of primers which can respectively anneal specifically to an upstream region and a downstream region of each of HLA-A, HLA-B, HLA-C, HLA-DQA1, HLA-DQB1, HLA-DPA1 and HLA-DPB1 gene in the nucleotide sequence for the human genome, and a set of primers which can respectively anneal specifically to exon-2 and a 3'-side non-translated region in HLA-DRB1; (2) a step of carrying out the PCR amplification of a sample to be tested (DNA) using the sets of primers; (3) a step of determining the nucleotide sequence for a PCR-amplified product; and (4) an optional step of carrying out the homology search in a data base.

18 Claims, 6 Drawing Sheets

Specification includes a Sequence Listing.

(56) References Cited

OTHER PUBLICATIONS

Lind C., et al., "Next-generation sequencing: the solution for high-resolution, unambiguous human leukocyte antigen typing," Human Immunology, vol. 71, pp. 1033-1042 (2010).
International Search Report dated Jul. 29, 2014 for PCT/JP2014/062433.
Seurynck K. et al., Use of 3' and 5' 1-35, Untranslated Region Polymorphism of Class I HLA-B to Determine Full Length Nucleotide Sequences, Human Immunology, 1997, vol. 55, No. Suppl. 1, p. 28.
Liu X. et al., Catalog of 162 single nucleotide 1-35 polymorphisms (SNPs) in a 4.7-kb region of the HLA-DP loci in southern Chinese ethnic groups, Journal of Human Genetics, 2004, vol. 49, p. 73-79.
Zhu F. et al., Analysis for complete genomic sequence of HLA-B and HLA-C alleles in the Chinese Han population, International Journal of Immunogenetics, May 17, 2011 (published online), vol. 38, p. 281-284.
International Search Report dated Aug. 7, 2012 for PCT/JP2012/062743.
Chinese Office Action dated Nov. 15, 2014 for Application No. 201280036108.5.
Zhu, et al. "Analysis of the complete genomic sequence of HLA-A alleles in the Chinese Han population," International Journal of Immunogenetics 26, 2009, 351-360.
Communication pursuant to Rule 164(1) EPC for Application No. 12814318.7.
Bentley, et al. "High-resolution, high-throughput HLA genotyping by next-generation sequencing." Tissue antigens 74.5 (2009): 393-403.
Gabriel, et al. "Rapid high-throughput human leukocyte antigen typing by massively parallel pyrosequencing for high-resolution allele identification." Human immunology 70.11 (2009): 960-964.
Dunn, et al. "DNA sequencing as a tissue-typing tool." Pediatric Hematology: Methods and Protocols (2004): 233-246.
Von Salomé, Jenny, Ulf Gyllensten, and Tomas F. Bergström. "Full-length sequence analysis of the HLA-DRB1 locus suggests a recent origin of alleles." Immunogenetics 59.4 (2007): 261-271.
Lowe, Todd, et al. "A computer program for selection of oligonucleotide primers for polymerase chain reactions." Nucleic Acids Research 18.7 (1990): 1757-1761.
Magor, Katharine E., et al. "Natural inactivation of a common HLA allele (A*2402) has occurred on at least three separate occasions." The Journal of Immunology 158.11 (1997): 5242-5250.
Genbank Accession No. NG_029217.1, "Homo sapiens major histocompatibility complex, class I, A (HLA-A)"; (GI: 338827610, available Jun. 20, 2011, retrieved on Sep. 25, 2015).
Genbank Accession No. L47206.1, "Homo sapiens MHC leukocyte antigen (HLA-A) gene, HLA-A*2401 allele, complete cds"; (GI: 6692988, available on Jan. 14, 2000, retrieved on Sep. 25, 2015).
Genbank Accession No. NT_007592.15"*Homo sapiens* chromosome 6 genomic contig, GRCh37.p13 Primary Assembly"; (available Jun. 10, 2009, retrieved on Sep. 23, 2015).
Office action in related U.S. Appl. No. 14/233,909, dated Oct. 2, 2015.

\* cited by examiner

METHOD AND KIT FOR DNA TYPING OF HLA GENE

CROSS-REFERENCE TO RELATED APPLICATIONS

This application is a divisional of application Ser. No. 14/233,909, filed Feb. 19, 2014, which is a national stage application of International Application PCT/JP2012/062743, filed May 18, 2012, and which claims priority of Japan application no. 2011-159832, all of which are hereby incorporated by reference.

TECHNICAL FIELD

The present invention relates to a method and a kit for DNA typing of a HLA gene using a massive parallel sequencer.

BACKGROUND ART

The human leucocyte antigen (HLA), which represents major human histocompatibility complex (MHC), presents peptides derived from foreign proteins such as pathogens and peptides derived from self-proteins to T cells. In this manner, HLA is deeply involved in induction of immunological responses. As major HLAs, six types of antigens are known, namely, class I molecules (HLA-A, HLA-B, HLA-C), which is expressed in almost all cells, and class II molecules (HLA-DR, HLA-DQ, HLA-DP), which is expressed mainly in immune cells.

The HLA class I antigen consists of a highly polymorphic α chain and a substantially non-polymorphic β2-microglobulin; whereas the HLA class II antigen consists of a highly polymorphic β chain and a less polymorphic α chain. The α chains of class I molecules are encoded by HLA-A, HLA-B and HLA-C genes. The β chains of class II antigens are encoded by HLA-DRB1, HLA-DQB1 and HLA-DPB1 genes, whereas the α chains are encoded by HLA-DRA1, HLA-DQA1 and HLA-DPA1 genes. In a gene level, in HLA class I antigens, exon 2 and exon 3 of a gene encoding an α chain are highly polymorphic; whereas, in HLA class II antigens, exon 2 of a gene encoding a β chain is highly polymorphic.

A gene region encoding a HLA is located on short arm of human chromosome 6 at 6p21.3. A Class I region (HLA-A, HLA-C and HLA-B, etc.), a class III region and a class II region (HLA-DRA, HLA-DRB1, HLA-DQA1, HLA-DQB1, HLA-DPA1, HLA-DPB1, etc.) are arranged in this order from the telomere side toward the centromere side. Many genes are encoded at an extremely high density and association of these genes with transfusion, transplantation and various diseases have been reported. In the class III region, no HLA genes are present and genes of complement components and tumor necrosis factors (TNF), etc. are present.

In a HLA-DRB gene region encoding a β chain of a HLA-DR antigen, it has been confirmed that 5 types of structural polymorphisms are present. In DR1 type and DR10 type, pseudogenes such as HLA-DRB6 and HLA-DRB9 in addition to HLA-DRB1 are located on the same chromosome. In DR2 type, a HLA-DRB5 (DR51) gene and pseudogenes such as HLA-DRB6 and HLA-DRB9 in addition to HLA-DRB1 are located on the same chromosome. In DR3, DR5 and DR6 types, a HLA-DRB3 (DR52) gene and pseudogenes such as HLA-DRB2 and HLA-DRB9 in addition to HLA-DRB1 are located on the same chromosome. In DR4, DR7 and DR9 types, a HLA-DRB4 (DR53) gene and pseudogenes such as HLA-DRB7, HLA-DRB8 and HLA-DRB9 in addition to HLA-DRB1 are located on the same chromosome. In contrast to these, in DR8 type, no HLA-DRB genes except HLA-DRB1 are located on the same chromosome.

In the exon of each allele, a plurality of regions exhibiting polymorphism are present. In many cases, a nucleotide sequence (amino acid sequence) present in a certain polymorphic region is commonly present in a plurality of alleles. In short, each HLA allele is specified by a plurality of polymorphic regions in combination. In a HLA class I antigen, not only a polymorphic region in the exon but also exon 2 or exon 3 having the same nucleotide sequence is sometimes commonly present in a plurality of alleles.

Since a highly polymorphic region is present in a HLA, the number of types of alleles is known to be extremely large and notation of them has been defined: i.e., a first field (two-digit level) is for discrimination of serologic HLA types, a second field (4-digit level) is for discrimination of alleles having an amino acid substitution in the same serologic HLA type, a third field (6-digit level) is for discrimination of alleles having a base substitution not accompanying an amino acid mutation and a fourth field (8-digit level) is for discrimination of alleles having a base substitution in an intron, which is out of the genetic region encoding a HLA molecule.

In bone marrow transplantation, it is said that if the HLA type of a patient seeking to receive a transplant completely matches the HLA type of a donor at a 4-digit level, the success rate of transplantation improves and a severe GVHD frequency reduces. Conversely, if the HLA types do not match at a 4 digit level, a risk of causing a failure such as a rejection response increases. Accordingly, accurate and highly precise HLA typing is extremely important also in a clinical point of view.

As a method for DNA typing in a HLA gene, a SBT (sequence based typing) method and a SSO (Sequence Specific Oligonucleotide)-Luminex method based on a polymerase chain reaction (PCR) are in mainstream.

These conventional DNA typing methods have an advantage in that typing of many samples is quickly performed; however, sometimes fail to accurately determine a polymorphic region and cis/trans positional relationship of exons on a chromosome in the case of a class I gene. Because of this, phase ambiguity occurs, highly precise HLA typing was sometimes not easily performed.

Since the conventional methods are DNA typing methods using PCR mainly based on exon regions of each gene, base substitutions in an intron region and a promoter region are overlooked, with the result that there was a risk of failure in detection of a null allele, which has the same gene structure as other HLA expressing genes but is suppressed in expression.

RELATED ART

Patent Document

Patent Document 1: JP H11-216000 A

Non Patent Document

Non Patent Document 1: Lind C., et al., Human Immunology, Vol. 71, Pages 1033-1042 (2010)

SUMMARY OF INVENTION

Technical Problem

An object of the present invention is to provide a method and a kit for highly precise DNA typing in which ambiguity derived from phase ambiguity is eliminated.

Solution to Problem

The present inventors newly conceived an idea of newly designing a PCR primer capable of specifically amplifying genes of HLAs such as HLA class I molecules including HLA-A, HLA-B and HLA-C and HLA class II molecules including HLA-DRB1, HLA-DQA1, HLA-DQB1, HLA-DPA1 and HLA-DPB1, setting suitable PCR conditions and applying a massive parallel sequencing technique. Based on the new idea, they repeatedly studied with a view to attaining the above object. As a result, they accomplished the present invention.

More specifically, the present invention provides a method for DNA typing of HLA, including the following steps:

(1) a step of preparing a set of primers which respectively anneal specifically to an upstream region and a downstream region of each of HLA-A, HLA-B, HLA-C, HLA-DQA1, HLA-DQB1, HLA-DPA1 and HLA-DPB1 genes in human genome sequence, and a set of primers which respectively anneal specifically to exon 2 and a 3' untranslated region of HLA-DRB1;

(2) a step of amplifying a test sample (DNA) by a PCR using the sets of primers;

(3) a step of determining the nucleotide sequences of PCR amplified products; and (4) a step of carrying out a homology search within a database.

Advantageous Effects of Invention

The method of the present invention, since it provides all nucleotide sequences required for DNA typing of a HLA gene from a single molecule, is an ultimate DNA typing method in which phase ambiguity due to unclear cis/trans positional relationship is eliminated. Owing to this, highly precise matching of HLAs between a patient seeking to receive a transplant and a donor candidate upon transplantation is realized.

Since all nucleotide sequences of a HLA gene including the peripheral regions such as a promoter region, exon regions and intron regions are determined, a null allele, which is not expressed at all or suppressed in expression, and a novel allele can be detected.

MODES FOR CARRYING OUT THE INVENTION

Now, the DNA typing method of the present invention will be more specifically described step by step.

(1) Step of Preparing a Primer Set

In the DNA typing method of the present invention, first, a set of primers which respectively anneal specifically to an upstream region and a downstream region of each of HLA-A, HLA-B, HLA-C, HLA-DQA1, HLA-DQB1, HLA-DPA1 and HLA-DPB1 genes in the human genome sequence and a set of primers which respectively anneal specifically to exon 2 and a 3' untranslated region of HLA-DRB1 are prepared.

Figure 1:
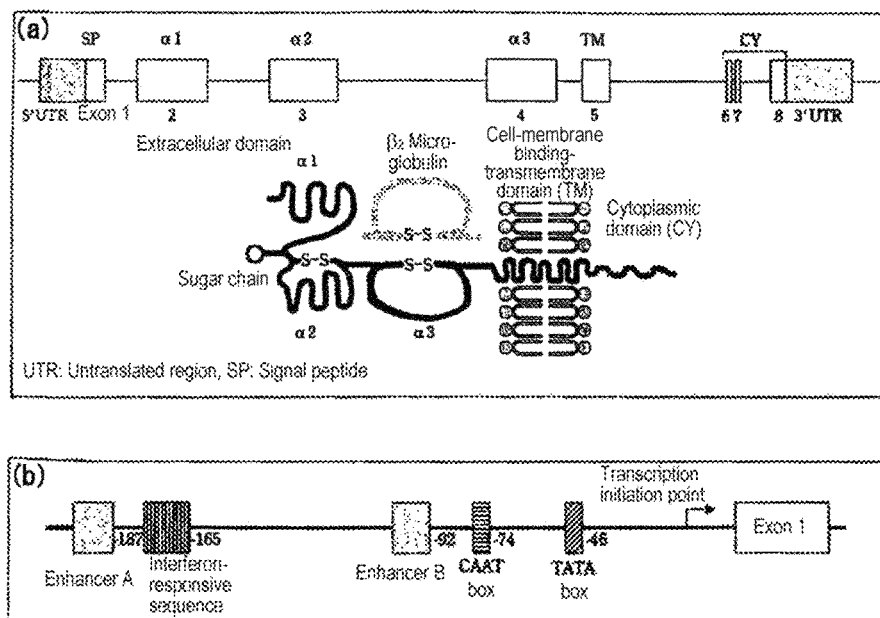
FIG. 1 (*a*) A diagram showing the relationship between the structure of a HLA class I gene and the structure of HLA class I molecule; and (*b*) A diagram showing the structure of a promoter region of a HLA class I gene, cited from "Transplantation/transfusion Examination", supervised by Hidetoshi Inoko, Takehiko Sasazuki and Takeo Juuji, Kodan-sha Scientific, 2004, page 35.
Figure 2:
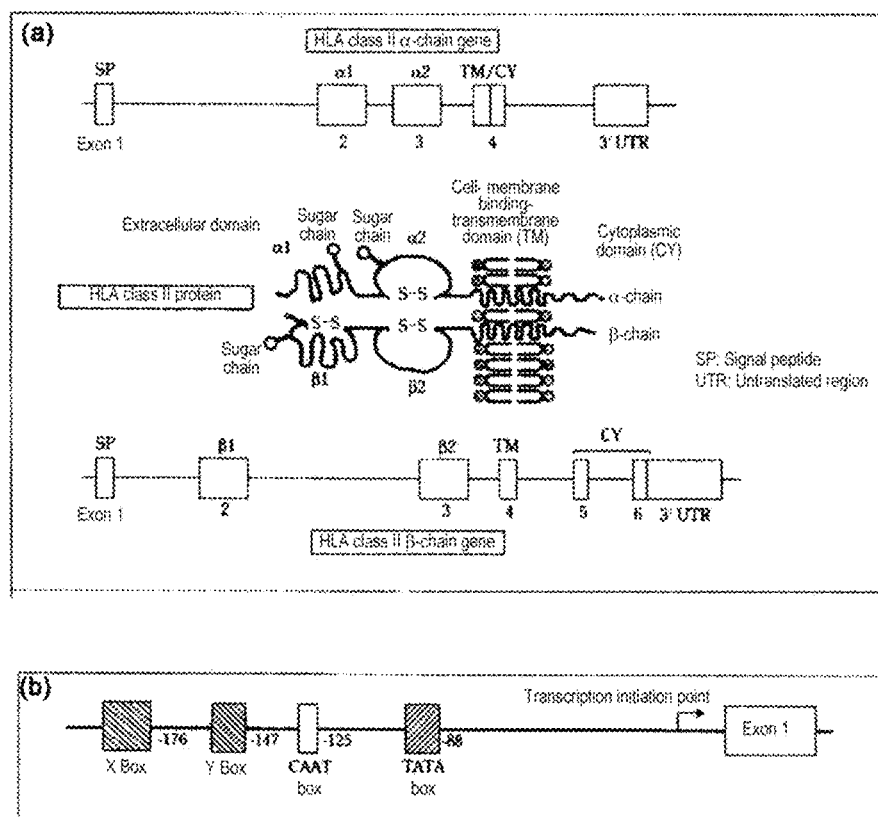
FIG. 2 (*a*) A diagram showing the relationship between the structure of a HLA class II gene and the structure of HLA class II molecule; and (*b*) A diagram showing the structure of a promoter region of a HLA class II gene, cited from "Transplantation/transfusion Examination", supervised by Hidetoshi Inoko, Takehiko Sasazuki and Takeo Juuji, Kodan-sha Scientific, 2004, pages 46 and 47.
Figure 3:
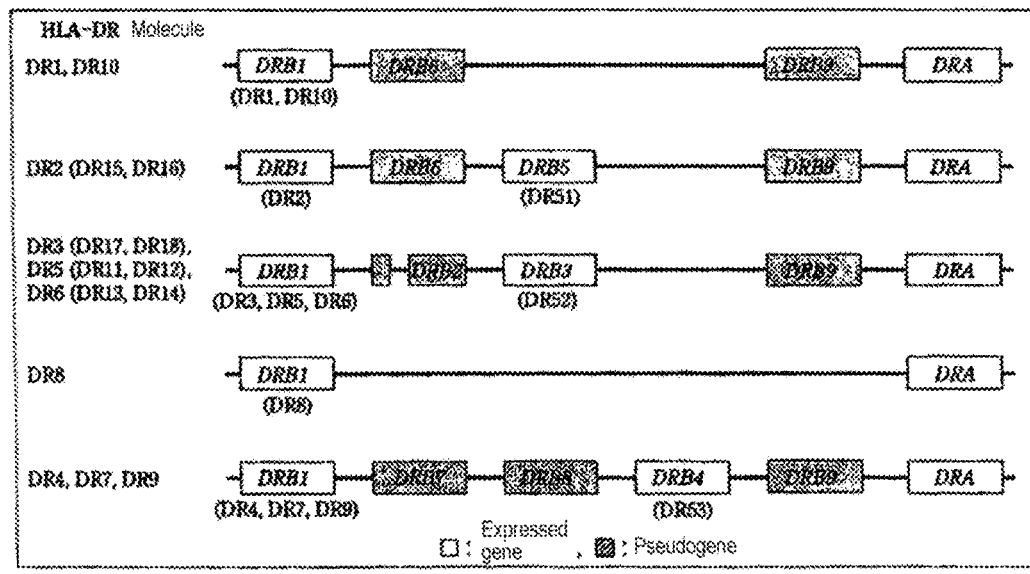
FIG. 3 A diagram showing a HLA-DR gene region, cited from "Transplantation/transfusion Examination", supervised by Hidetoshi Inoko, Takehiko Sasazuki and Takeo Juuji, Kodan-sha Scientific, 2004, page 48.

The genome sequence of human chromosome 6 (6p21.3) in which a HLA gene is present has been already elucidated and association of the gene structure and the structure of an expression product (HLA molecule) has been known (see FIG. 1 and FIG. 2).

More specifically, genes of HLA-A, HLA-B and HLA-C, which are called classic HLA class I molecules, each contain 7 or 8 exons (FIG. 1(*a*)). Outside of exon 1, two types of enhancers and a promoter region are present to control expression (FIG. 1 (*b*)).

It is further known that many polymorphic regions are present in exon 2, 3 and 4. Thus, PCR was performed by using primers prepared particularly based on exon 2 and 3 in conventional DNA typing methods. Accordingly, a problem of phase ambiguity has occurred as mentioned above.

In the meantime, the genes of HLA-DR, HLA-DQ and HLA-DP, which are called classic HLA class II molecules, consist of α chains and β chains, whose genes each contain 5 to 6 exons (FIG. 2 (*a*)). Outside of exon 1, a promoter region is present to control expression (FIG. 2 (*b*)).

It is further known that many polymorphic regions are present in exon 2 and 3. Thus, PCR was performed by using primers prepared particularly based on exon 2 in conventional DNA typing methods. Accordingly, a problem of phase ambiguity occurred as mentioned above.

In the present invention, a set of primers which can amplify (by PCR) all regions of a gene (including not only exons but also introns, 5' and 3' untranslated regions and a promoter region) in each of classic class I molecules (HLA-A, HLA-B, HLA-C) and classic class II molecules (HLA-DQA1, HLA-DQB1, HLA-DPA1 and HLA-DPB1); and a set of primers which can amplify (by PCR) the gene regions of HLA-DRB1 including exon 2 to a 3' untranslated region are prepared, and PCR products obtained by PCR amplification using the sets of primers are subjected to next-generation sequencing (described later). Therefore, uncertainty such as phase ambiguity can be eliminated and the presence or absence of a null allele can be accurately detected.

Specifically, PCR primer sets listed in Table 1 to Table 4 below are prepared.

In Table 1, SEQ ID Nos. 1 to 3 represent a set of PCR primers specifically amplifying a HLA-A gene, which is an α chain of MHC class I. These primers of the set are nucleotide sequences located at positions, which correspond to the upstream and downstream of all regions of a HLA-A gene (including promoter, exons and introns), and sandwich the all regions, in the human genome sequence (Reference sequence: hg19).

SEQ ID No. 1 has a nucleotide sequence corresponding to the 29,909,487th position to the 29,909,514th position in a human genome sequence (Reference sequence: hg19).

SEQ ID No. 2 has a nucleotide sequence corresponding to the 29,909,487th position to the 29,909,514th position in a human genome sequence (Reference sequence: hg19).

In Table 1, SEQ ID Nos. 6 to 8 represent a set of PCR primers specifically amplifying a HLA-C gene, which is an α chain of MHC class I. These primers of the set are nucleotide sequences located at positions, which correspond to the upstream and downstream of all regions of a HLA-C gene (including promoter, exons and introns), and sandwich the all regions, in the human genome sequence (Reference sequence: hg19).

SEQ ID No. 6 has a complementary nucleotide sequence to a nucleotide sequence corresponding to the 31,240,868th position to the 31,240,892nd position in a human genome sequence (Reference sequence: hg19).

SEQ ID No. 7 has a complementary nucleotide sequence to a nucleotide sequence corresponding to the 31,240,868th position to the 31,240,892nd position in a human genome sequence (Reference sequence: hg19).

SEQ ID No. 8 has a nucleotide sequence corresponding to the 31,236,991st position to the 31,236,114th position in a human genome sequence (Reference sequence: hg19).

The length of a PCR product obtained by using these primer sets is estimated as about 4,800 bases (bp).

TABLE 1

| HLA-class I gene | Name of primer | Length of primer (mer) | Primer sequence (5'-3') | Sequence ID No. | Estimated length of PCR product (bp) |
| --- | --- | --- | --- | --- | --- |
| HLA-A | HLA-A_F1 | 28 | AACTCAGAGCTAAGGAATGATGGCAAAT | 1 | 5,466 |
|  | HLA-A_F2 | 28 | AACTCAGAGCTATGGAATGATGGTAAAT | 2 |  |
|  | HLA-A_R1 | 28 | ATATAACCATCATCGTGTCCCAAGGTTC | 3 |  |
| HLA-B | HLA-B_F1 | 25 | CCCGGTTGCAATAGACAGTAACAAA | 4 | 4,609 |
|  | HLA-B_R1 | 24 | GGGTCCAATTTCACAGACAAATGT | 5 |  |
| HLA-C | HLA-C_F1 | 25 | TGCTTAGATGTGCATAGTTCACGAA | 6 | 4,802 |
|  | HLA-C_F2 | 25 | TGCTTAGATGTGCATGTTCCGGAA | 7 |  |
|  | HLA-C_R1 | 24 | TGGACCCAATTTTACAAACAAATA | 8 |  |

SEQ ID No. 3 has a complementary nucleotide sequence to a nucleotide sequence corresponding to the 29,914,925th position to the 29,914,952nd position in a human genome sequence (Reference sequence: hg19).

The length of a PCR product obtained by using these primer sets is estimated as about 5,500 bases (bp).

In Table 1, SEQ ID Nos. 4 and 5 represent a set of PCR primers specifically amplifying a HLA-B gene, which is an α chain of MHC class I. These primers of the set are nucleotide sequences located at positions, which correspond to the upstream and downstream of all regions of a HLA-B gene (including promoter, exons and introns), and sandwich the all regions, in the human genome sequence (Reference sequence: hg19).

SEQ ID No. 4 has a complementary nucleotide sequence to a nucleotide sequence corresponding to the 31,325,796th position to the 31,325,820th position in a human genome sequence (Reference sequence: hg19).

SEQ ID No. 5 has a nucleotide sequence corresponding to the 31,321,212nd position to the 31,321,235th position in a human genome sequence (Reference sequence: hg19).

The length of a PCR product obtained by using these primer sets is estimated as about 4,600 bases (bp).

In Table 2, SEQ ID Nos. 9 to 11 represent a set of PCR primers of specifically amplifying a HLA-DR1 subtype gene of a HLA-DRB1 gene, which is a β chain of MHC class II. These primers of the set are nucleotide sequences located at positions, which correspond to the upstream and downstream of exon 2 to a 3' untranslated region of a HLA-DRB1 gene and sandwich the exon 2 to a 3' untranslated region in the human genome sequence (Reference sequence: hg19).

SEQ ID No. 9 has a complementary nucleotide sequence to a nucleotide sequence corresponding to the 32,552,131st position to the 32,552,156th position in a human genome sequence (Reference sequence: hg19).

SEQ ID No. 10 has a complementary nucleotide sequence to a nucleotide sequence corresponding to the 32,552,131st position to the 32,552,156th position in a human genome sequence (Reference sequence: hg19).

SEQ ID No. 11 has a nucleotide sequence corresponding to the 32,546,609th position to the 32,546,629th position in a human genome sequence (Reference sequence: hg19).

The length of a PCR product obtained by using these primer sets is estimated as about 5,200 bases (bp).

In Table 2, SEQ ID Nos. 31 and 32 represent a set of PCR primers of specifically amplifying HLA-DR1, HLA-DR4, HLA-DR6 (DR13) and a HLA-DR10 subtype gene of a HLA-DRB1 gene, which is a β chain of MHC class II. These primers of the set are nucleotide sequences located at positions, which correspond to the upstream and downstream of a 5' untranslated region to exon 2 of a HLA-DRB1 gene and sandwich the 5' untranslated region to exon 2 in the human genome sequence (Reference sequence: hg19).

SEQ ID No. 31 has a complementary nucleotide sequence to a nucleotide sequence corresponding to the 32,558,110th position to the 32,558,133rd position in a human genome sequence (Reference sequence: hg19).

SEQ ID No. 32 has a nucleotide sequence corresponding to the 32,551,974th position to the 32,551,999th position in a human genome sequence (Reference sequence: hg19).

The lengths of PCR products obtained by using these primer sets are estimated as about 6,100 bases (bp) in the case of a HLA-DR1 subtype, about 9,100 bases (bp) in the case of a HLA-DR4 subtype, about 8,900 bases (bp) in the case of a HLA-DR6 (DR13) subtype and about 8,900 bases (bp) in the case of a HLA-DR10 subtype.

In Table 2, SEQ ID Nos. 11 and 12 represent a set of PCR primers of specifically amplifying a HLA-DR2 subtype gene of a HLA-DRB1 gene, which is a β chain of MHC class II. These primers of the set are nucleotide sequences located at positions, which correspond to the upstream and downstream of exon 2 to a 3' untranslated region of a HLA-DRB1 gene and sandwich the exon 2 to a 3' untranslated region in the human genome sequence (Reference sequence: hg19).

SEQ ID No. 11 is as defined above.

SEQ ID No. 12 has a complementary nucleotide sequence to a nucleotide sequence corresponding to the 32,552,130th position to the 32,552,151st position in a human genome sequence (Reference sequence: hg19).

The length of a PCR product obtained by using these primer sets is estimated as about 5,500 bases (bp).

In Table 3, SEQ ID Nos. 31 and 33 represent a set of PCR primers of specifically amplifying a HLA-DR2 (DR15) subtype gene of a HLA-DRB1 gene, which is a β chain of MHC class II. These primers of the set are nucleotide sequences located at positions, which correspond to the upstream and downstream of a 5' untranslated region to exon 2 of a HLA-DRB1 gene and sandwich the 5' untranslated region to exon 2 in the human genome sequence (Reference sequence: hg19).

SEQ ID No. 31 is as defined above.

SEQ ID No. 33 has a nucleotide sequence corresponding to the 32,551,974th position to the 32,551,999th position in a human genome sequence (Reference sequence: hg19).

The length of a PCR product obtained by using these primer sets is estimated as about 6,100 bases (bp).

In Table 2, SEQ ID Nos. 13 and 14 represent a set of PCR primers of specifically amplifying a HLA-DR3, HLA-DR5, HLA-DR6 and HLA-DR8 subtype gene of a HLA-DRB1 gene, which is a β chain of MHC class II. These primers of the set are nucleotide sequences located at positions, which correspond to the upstream and downstream of exon 2 to a 3' untranslated region of a HLA-DRB1 gene and sandwich the exon 2 to a 3' untranslated region in the human genome sequence (Reference sequence: hg19).

SEQ ID No. 13 has a complementary nucleotide sequence to a nucleotide sequence corresponding to the 32,552,137th position to the 32,552,160th position in a human genome sequence (Reference sequence: hg19).

SEQ ID No. 14 has a nucleotide sequence corresponding to the 32,546,609th position to the 32,546,629th position in a human genome sequence (Reference sequence: hg19).

The length of a PCR product obtained by using these primer sets is estimated as about 5,100 bases (bp).

In Table 2, SEQ ID Nos. 34 and 32 represent a set of PCR primers of specifically amplifying a HLA-DR3 subtype gene of a HLA-DRB1 gene, which is a β chain of MHC class II. These primers of the set are nucleotide sequences located at positions, which correspond to the upstream and downstream of a 5' untranslated region to exon 2 of a HLA-DRB1 gene and sandwich the 5' untranslated region to exon 2 in the human genome sequence (Reference sequence: hg19).

SEQ ID No. 34 has a complementary nucleotide sequence to a nucleotide sequence corresponding to the 32,558,110th position to the 32,558,133rd position in a human genome sequence (Reference sequence: hg19).

SEQ ID No. 32 is as defined above.

The length of a PCR product obtained by using these primer sets is estimated as about 8,900 bases (bp).

In Table 2, SEQ ID Nos. 15 and 16 represent a set of PCR primers of specifically amplifying a HLA-DR4 subtype gene of a HLA-DRB1 gene, which is a β chain of MHC class II. These primers of the set are nucleotide sequences located at positions, which correspond to the upstream and downstream of exon 2 to a 3' untranslated region of a HLA-DRB1 gene and sandwich the exon 2 to a 3' untranslated region in the human genome sequence (Reference sequence: hg19).

SEQ ID No. 15 has a complementary nucleotide sequence to a nucleotide sequence corresponding to the 32,552,131st position to the 32,552,157th position in a human genome sequence (Reference sequence: hg19).

SEQ ID No. 16 has a nucleotide sequence corresponding to the 32,546,609th position to the 32,546,629th position in a human genome sequence (Reference sequence: hg19).

The length of a PCR product obtained by using these primer sets is estimated as about 6,200 bases (bp).

In Table 2, SEQ ID Nos. 31 and 35 represent a set of PCR primers of specifically amplifying a HLA-DR5 (DR11) subtype gene of a HLA-DRB1 gene, which is a β chain of MHC class II. These primers of the set are nucleotide sequences located at positions, which correspond to the upstream and downstream of a 5' untranslated region to exon 2 of a HLA-DRB1 gene and sandwich the 5' untranslated region to exon 2 in the human genome sequence (Reference sequence: hg19).

SEQ ID No. 31 is as defined above.

SEQ ID No. 35 has a nucleotide sequence corresponding to the 32,551,974th position to the 32,551,999th position in a human genome sequence (Reference sequence: hg19).

The length of a PCR product obtained by using these primer sets is estimated as about 8,900 bases (bp).

In Table 2, SEQ ID Nos. 31 and 36 represent a set of PCR primers of specifically amplifying a HLA-DR5 (DR12) subtype gene of a HLA-DRB1 gene, which is a β chain of MHC class II. These primers of the set are nucleotide sequences located at positions, which correspond to the upstream and downstream of a 5' untranslated region to exon 2 of a HLA-DRB1 gene and sandwich the 5' untranslated region to exon 2 in the human genome sequence (Reference sequence: hg19).

SEQ ID No. 31 is as defined above.

SEQ ID No. 36 has a nucleotide sequence corresponding to the 32,551,974th position to the 32,551,999th position in a human genome sequence (Reference sequence: hg19).

The length of a PCR product obtained by using these primer sets is estimated as about 8,900 bases (bp).

TABLE 2

| HLA-class II gene | Name of primer | Length of primer (mer) | Primer sequence (5'-3') | Sequence ID No. | Estimated length of PCR product (bp) |
|---|---|---|---|---|---|
| HLA-DR1 | DR-E2-1.2-F | 26 | GCACGTTTCTTGTGGCAGCTTAAGTT | 9 | 5,199 |
|  | DR-E2-1.1-F | 26 | GCACGTTTCTTGTGGCAGCTAAAGTT | 10 |  |
|  | DR-E2-12-R | 21 | ATGCACGGGAGGCCATACGGT | 11 |  |
| HLA-DR1 | DRB_PE2-F1 | 24 | CTGCTGCTCCTTGAGGCATCCACA | 31 | 6,168 |
|  | DRB_PE2-R1 | 26 | CTTCTGGCTGTTCCAGTACTCGGCAT | 32 |  |
| HLA-DR2 | DR-E2-2-F | 22 | TTTCCTGTGGCAGCCTAAGAGG | 12 | 5,543 |
|  | DR-E2-12-R | 21 | ATGCACGGGAGGCCATACGGT | 11 |  |
| HLA-DR2 (DR15) | DRB_PE2-F1 | 24 | CTGCTGCTCCTTGAGGCATCCACA | 31 | 6,146 |
|  | DRB_PE2-R3 | 26 | CTTCTGGCTGTTCCAGTACTCAGCGT | 33 |  |
| HLA-DR3 | DR-E2-3568-F | 24 | CACAGCACGTTTCTTGGAGTACTC | 13 | 5,157 |
|  | DR-E2-3568-R | 21 | ATGCACAGGAGGCCATAGGGT | 14 |  |
| HLA-DR3 | DRB_PE2-F3 | 24 | CTGCTGCTCCCTGAGGCATCCACA | 34 | 8,894 |
|  | DRB_PE2-R1 | 26 | CTTCTGGCTGTTCCAGTACTCGGCAT | 32 |  |
| HLA-DR4 | DR-E2-4-F | 27 | AGCACGTTTCTTGGAGCAGGTTAAACA | 15 | 6,218 |
|  | DR-E2-4-R | 21 | ATGCATGGGAGGCAGGAAGCA | 16 |  |
| HLA-DR4 | DRB_PE2-F1 | 24 | CTGCTGCTCCTTGAGGCATCCACA | 31 | 9,159 |
|  | DRB_PE2-R1 | 26 | CTTCTGGCTGTTCCAGTACTCGGCAT | 32 |  |
| HLA-DR5 | DR-E2-3568-F | 24 | CACAGCACGTTTCTTGGAGTACTC | 13 | 5,172 |
|  | DR-E2-3568-R | 21 | ATGCACAGGAGGCCATAGGGT | 14 |  |
| HLA-DR5 (DR11) | DRB_PE2-F1 | 24 | CTGCTGCTCCTTGAGGCATCCACA | 31 | 8,888 |
|  | DRB_PE2-R4 | 26 | CTTCTGGCTGTTCCAGTACTCCTCAT | 35 |  |
| HLA-DR5 (DR12) | DRB_PE2-F1 | 24 | CTGCTGCTCCTTGAGGCATCCACA | 31 | 8,888 |
|  | DRB PE2-R2 | 26 | CTTCTGGCTGTTCCAGGACTCGGCGA | 36 |  |

In Table 3, SEQ ID Nos. 31 and 37 represent a set of PCR primers of specifically amplifying a HLA-DR6 (DR14) subtype gene of a HLA-DRB1 gene, which is a β chain of MHC class II. These primers of the set are nucleotide sequences located at positions, which correspond to the upstream and downstream of a 5' untranslated region to exon 2 of a HLA-DRB1 gene and sandwich the 5' untranslated region to exon 2 in the human genome sequence (Reference sequence: hg19).

SEQ ID No. 31 is as defined above.

SEQ ID No. 37 has a nucleotide sequence corresponding to the 32,551,974th position to the 32,551,999th position in a human genome sequence (Reference sequence: hg19).

The length of a PCR product obtained by using these primer sets is estimated as about 8,900 bases (bp).

In Table 3, SEQ ID Nos. 17 and 18 represent a set of PCR primers of specifically amplifying a HLA-DR7 subtype gene of a HLA-DRB1 gene, which is a β chain of MHC class II. These primers of the set are nucleotide sequences located at positions, which correspond to the upstream and downstream of exon 2 to a 3' untranslated region of a HLA-DRB1 gene and sandwich the exon 2 to a 3' untranslated region in the human genome sequence (Reference sequence: hg19).

SEQ ID No. 17 has a complementary nucleotide sequence to a nucleotide sequence corresponding to the 32,552,137th position to the 32,552,160th position in a human genome sequence (Reference sequence: hg19).

SEQ ID No. 18 has a nucleotide sequence corresponding to the 32,546,606th position to the 32,546,629th position in a human genome sequence (Reference sequence: hg19).

The length of a PCR product obtained by using these primer sets is estimated as about 5,100 bases (bp).

In Table 3, SEQ ID Nos. 38 and 36 represent a set of PCR primers of specifically amplifying a HLA-DR7 and HLA-DR9 subtype gene of a HLA-DRB1 gene, which is a β chain of MHC class II. These primers of the set are nucleotide sequences located at positions, which correspond to the upstream and downstream of a 5' untranslated region to exon 2 of a HLA-DRB1 gene and sandwich the 5' untranslated region to exon 2 in the human genome sequence (Reference sequence: hg19).

SEQ ID No. 38 has a complementary nucleotide sequence to a nucleotide sequence corresponding to the 32,558,110th position to the 32,558,133rd position in a human genome sequence (Reference sequence: hg19).

SEQ ID No. 36 is as defined above.

The length of a PCR product obtained by using these primer sets is estimated as about 11,400 bases (bp).

In Table 3, SEQ ID Nos. 31 and 39 represent a set of PCR primers of specifically amplifying a HLA-DR8 subtype gene of a HLA-DRB1 gene, which is a β chain of MHC class II. These primers of the set are nucleotide sequences located at positions, which correspond to the upstream and downstream of a 5' untranslated region to exon 2 of a HLA-DRB1 gene and sandwich the 5' untranslated region to exon 2 in the human genome sequence (Reference sequence: hg19).

SEQ ID No. 31 is as defined above.

SEQ ID No. 39 has a nucleotide sequence corresponding to the 32,551,974th position to the 32,551,999th position in a human genome sequence (Reference sequence: hg19).

The length of a PCR product obtained by using these primer sets is estimated as about 8,900 bases (bp).

In Table 3, SEQ ID Nos. 19 and 20 represent a set of PCR primers of specifically amplifying a HLA-DR9 subtype gene of a HLA-DRB1 gene, which is a β chain of MHC class II. These primers of the set are nucleotide sequences located at positions, which correspond to the upstream and downstream of exon 2 to a 3' untranslated region of a HLA-DRB1 gene and sandwich the exon 2 to a 3' untranslated region in the human genome sequence (Reference sequence: hg19).

SEQ ID No. 19 has a complementary nucleotide sequence to a nucleotide sequence corresponding to the 32,552,137th position to the 32,552,160th position in a human genome sequence (Reference sequence: hg19).

SEQ ID No. 20 has a nucleotide sequence corresponding to the 32,546,609th position to the 32,546,629th position in a human genome sequence (Reference sequence: hg19).

The length of a PCR product obtained by using these primer sets is estimated as about 5,100 bases (bp).

In Table 3, SEQ ID Nos. 21 and 22 represent a set of PCR primers of specifically amplifying a HLA-DR10 subtype gene of a HLA-DRB1 gene, which is a β chain of MHC class II. These primers of the set are nucleotide sequences located at positions, which correspond to the upstream and downstream of exon 2 to a 3' untranslated region of a HLA-DRB1 gene and sandwich the exon 2 to a 3' untranslated region in the human genome sequence (Reference sequence: hg19).

SEQ ID No. 21 has a complementary nucleotide sequence to a nucleotide sequence corresponding to the 32,552,137th position to the 32,552,159th position in a human genome sequence (Reference sequence: hg19).

SEQ ID No. 22 has a nucleotide sequence corresponding to the 32,546,403rd position to the 32,546,435th position in a human genome sequence (Reference sequence: hg19).

The length of a PCR product obtained by using these primer sets is estimated as about 5,400 bases (bp).

TABLE 3

| HLA-class II gene | Name of primer | Length of primer (mer) | Primer sequence (5'-3') | Sequence ID No. | Estimated length of PCR product (bp) |
|---|---|---|---|---|---|
| HLA-DR6 | DR-E2-3568-F | 24 | CACAGCACGTTTCTTGGAGTACTC | 13 | 5,179 |
|  | DR-E2-3568-R | 21 | ATGCACAGGAGGCCATAGGGT | 14 |  |
| HLA-DR6 (DR13) | DRB_PE2-F1 | 24 | CTGCTGCTCCTTGAGGCATCCACA | 31 | 8,895 |
|  | DRB_PE2-R1 | 26 | CTTCTGGCTGTTCCAGTACTCGGCAT | 32 |  |
| HLA-DR6 (DR14) | DRB_PE2-F1 | 24 | CTGCTGCTCCTTGAGGCATCCACA | 31 | 8,895 |
|  | DRB_PE2-R5 | 26 | CTTCTGGCTGTTCCAGTGCTCCGCAG | 37 |  |
| HLA-DR7 | DR-E2-7-F4 | 24 | CACAGCACGTTTCCTGTGGCAGGG | 17 | 5,070 |
|  | DR-E2-7-R2 | 24 | CAGATGCATGGGAGGCAGGAAGCG | 18 |  |
| HLA-DR7 | DRB_PE2-F2 | 24 | CTGCTACTCCTTGAGGCATCCACA | 38 | 11,409 |
|  | DRB_PE2-R2 | 26 | CTTCTGGCTGTTCCAGGACTCGGCGA | 36 |  |
| HLA-DR8 | DR-E2-3568-F | 24 | CACAGCACGTTTCTTGGAGTACTC | 13 | 5,167 |
|  | DR-E2-3568-R | 21 | ATGCACAGGAGGCCATAGGGT | 14 |  |
| HLA-DR8 | DRB_PE2-F1 | 24 | CTGCTGCTCCTTGAGGCATCCACA | 31 | 8,841 |
|  | DRB_PE2-R6 | 26 | CTTCTGGCTGTTCCAGTACTCGGCGC | 39 |  |

TABLE 3 -continued

| HLA-class II gene | Name of primer | Length of primer (mer) | Primer sequence (5'-3') | Sequence ID No. | Estimated length of PCR product (bp) |
|---|---|---|---|---|---|
| HLA-DR9 | DR-E2-9-F | 24 | CACAGCACGTTTCTTG AAGCAGGA | 19 | 5,067 |
|  | DR-E2-9-R | 21 | ATGCATGGGAGGCAGG AAGCG | 20 |  |
| HLA-DR9 | DRB_PE2-F2 | 24 | CTGCTACTCCTTGAGGC ATCCACA | 38 | 11,478 |
|  | DRB_PE2-R2 | 26 | CTTCTGGCTGTTCCAGG ACTCGGCGA | 36 |  |
| HLA-DR10 | DR-E2-10-F | 23 | ACAGCACGTTTCTTGG AGGAGGT | 21 | 5,354 |
|  | DR-E2-10-R | 33 | TGGAATGTCTAAAGCA AGCTATTTAACATATGT | 22 |  |
| HLA-DR10 | DRB_PE2-F1 | 24 | CTGCTGCTCCTTGAGGC ATCCACA | 31 | 8,888 |
|  | DRB_PE2-R1 | 26 | CTTCTGGCTGTTCCAGT ACTCGGCAT | 32 |  |

In Table 4, SEQ ID Nos. 23 and 24 represent a set of PCR primers specifically amplifying a HLA-DPA1 gene, which is an α chain of MHC class II. These primers of the set are nucleotide sequences located at positions, which correspond to the upstream and downstream of all regions of a HLA-DPA1 gene (including promoter, exons and introns), and sandwich the all regions, in the human genome sequence (Reference sequence: hg19).

SEQ ID No. 23 has a complementary nucleotide sequence to a nucleotide sequence corresponding to the 33,041,478th position to the 33,041,502nd position in a human genome sequence (Reference sequence: hg19).

SEQ ID No. 24 has a nucleotide sequence corresponding to the 33,031,888th position to the 33,031,911st position in a human genome sequence (Reference sequence: hg19).

The length of a PCR product obtained by using these primer sets is estimated as about 9,600 bases (bp).

In Table 4, SEQ ID Nos. 40 and 41 represent a set of PCR primers specifically amplifying a HLA-DPA1 gene, which is an α chain of MHC class II. These primers of the set are nucleotide sequences located at positions, which correspond to the upstream and downstream of all regions of a HLA-DPA1 gene (including promoter, exons and introns), and sandwich the all regions, in the human genome sequence (Reference sequence: hg19).

SEQ ID No. 40 has a complementary nucleotide sequence to a nucleotide sequence corresponding to the 33,041,573rd position to the 33,041,596th position in a human genome sequence (Reference sequence: hg19).

SEQ ID No. 41 has a nucleotide sequence corresponding to the 33,031,888th position to the 33,031,912nd position in a human genome sequence (Reference sequence: hg19).

The length of a PCR product obtained by using these primer sets is estimated as about 9,600 bases (bp).

In Table 4, SEQ ID Nos. 25 and 26 represent a set of PCR primers specifically amplifying a HLA-DPB1 gene, which is a β chain of MHC class II. These primers of the set are nucleotide sequences located at positions, which correspond to the upstream and downstream of all regions of a HLA-DPB1 gene (including promoter, exons and introns), and sandwich the all regions, in the human genome sequence (Reference sequence: hg19).

SEQ ID No. 25 has a nucleotide sequence corresponding to the 33,043,056th position to the 33,043,079th position in a human genome sequence (Reference sequence: hg19).

SEQ ID No. 26 has a complementary nucleotide sequence to a nucleotide sequence corresponding to the 33,055,476th position to the 33,055,499th position in a human genome sequence (Reference sequence: hg19).

The length of a PCR product obtained by using these primer sets is estimated as about 12,400 bases (bp).

In Table 4, SEQ ID Nos. 42 and 43 represent a set of PCR primers of specifically amplifying a HLA-DPB1 gene, which is a β chain of MHC class II. These primers of the set are nucleotide sequences located at positions, which correspond to the upstream and downstream of a 5' untranslated region to exon 2 of a HLA-DPB1 gene and sandwich the 5' untranslated region to exon 2 in the human genome sequence (Reference sequence: hg19).

SEQ ID No. 42 has a nucleotide sequence corresponding to the 33,043,168th position to the 33,043,191st position in a human genome sequence (Reference sequence: hg19).

SEQ ID No. 43 has a complementary nucleotide sequence to a nucleotide sequence corresponding to the 33,049,084th position to the 33,049,107th position in a human genome sequence (Reference sequence: hg19).

The length of a PCR product obtained by using these primer sets is estimated as about 5,900 bases (bp).

In Table 4, SEQ ID Nos. 44 and 45 represent a set of PCR primers of specifically amplifying a HLA-DPB1 gene, which is a β chain of MHC class II. These primers of the set are nucleotide sequences located at positions, which correspond to the upstream and downstream of exon 2 to a 3' untranslated region of a HLA-DPB1 gene and sandwich the exon 2 to a 3' untranslated region in the human genome sequence (Reference sequence: hg19).

SEQ ID No. 44 has a nucleotide sequence corresponding to the 33,048,182nd position to the 33,048,207th position in a human genome sequence (Reference sequence: hg19).

SEQ ID No. 45 has a complementary nucleotide sequence to a nucleotide sequence corresponding to the 33,055,428th position to the 33,055,453rd position in a human genome sequence (Reference sequence: hg19).

The length of a PCR product obtained by using these primer sets is estimated as about 7,200 bases (bp).

In Table 4, SEQ ID Nos. 27 and 28 represent a set of PCR primers specifically amplifying a HLA-DQA1 gene, which is an α chain of MHC class II. These primers of the set are nucleotide sequences located at positions, which correspond to the upstream and downstream of all regions of a HLA-DQA1 gene (including promoter, exons and introns), and sandwich the all regions, in the human genome sequence (Reference sequence: hg19).

SEQ ID No. 27 has a nucleotide sequence corresponding to the 32,604,318th position to the 32,604,338th position in a human genome sequence (Reference sequence: hg19).

SEQ ID No. 28 has a complementary nucleotide sequence to a nucleotide sequence corresponding to the 32,611,681st position to the 32,611,701st position in a human genome sequence (Reference sequence: hg19).

The length of a PCR product obtained by using these primer sets is estimated as about 7,400 bases (bp).

In Table 4, SEQ ID Nos. 46 and 47 represent a set of PCR primers specifically amplifying a HLA-DQA1 gene, which is an α chain of MHC class II. These primers of the set are nucleotide sequences located at positions, which correspond to the upstream and downstream of all regions of a HLA-DQA1 gene (including promoter, exons and introns), and sandwich the all regions, in the human genome sequence (Reference sequence: hg19).

SEQ ID No. 46 has a nucleotide sequence corresponding to the 32,604,469th position to the 32,604,488th position in a human genome sequence (Reference sequence: hg19).

SEQ ID No. 47 has a complementary nucleotide sequence to a nucleotide sequence corresponding to the 32,611,936th position to the 32,611,956th position in a human genome sequence (Reference sequence: hg19).

The length of a PCR product obtained by using these primer sets is estimated as about 7,400 bases (bp).

In Table 4, SEQ ID Nos. 29 and 30 represent a set of PCR primers specifically amplifying a HLA-DQB1 gene, which is a β chain of MHC class II. These primers of the set are nucleotide sequences located at positions, which correspond to the upstream and downstream of all regions of a HLA-DQB1 gene (including promoter, exons and introns), and sandwich the all regions, in the human genome sequence (Reference sequence: hg19).

SEQ ID No. 29 has a nucleotide sequence corresponding to the 32,626,545th position to the 32,626,568th position in a human genome sequence (Reference sequence: hg19).

SEQ ID No. 30 has a complementary nucleotide sequence to a nucleotide sequence corresponding to the 32,635,612nd position to the 32,635,637th position in a human genome sequence (Reference sequence: hg19).

The length of a PCR product obtained by using these primer sets is estimated as about 9,100 bases (bp).

In Table 4, SEQ ID Nos. 29, 30 and 48 to 50 represent a set of PCR primers specifically amplifying a HLA-DQB1 gene, which is a β chain of MHC class II. These primers of the set are nucleotide sequences located at positions, which correspond to the upstream and downstream of all regions of a HLA-DQB1 gene (including promoter, exons and introns), and sandwich the all regions, in the human genome sequence (Reference sequence: hg19).

SEQ ID Nos. 29 and 48 have a nucleotide sequence corresponding to the 32,626,545th position to the 32,626,568th position in a human genome sequence (Reference sequence: hg19).

SEQ ID Nos. 30, 49 and 50 have a complementary nucleotide sequence to a nucleotide sequence corresponding to the 32,635,612nd position to the 32,635,637th position in a human genome sequence (Reference sequence: hg19).

The length of a PCR product obtained by using these primer sets is estimated as about 9,100 bases (bp).

TABLE 4

| HLA-class II gene | Name of primer | Length of primer (mer) | Primer sequence (5'-3') | Sequence ID No. | Estimated length of PCR product (bp) |
|---|---|---|---|---|---|
| HLA-DPA1 | DPA1-F2 | 25 | TGATTTCTCTGATAGGTGAATCCCA | 23 | 9,615 |
|  | DPA1-R2 | 24 | TTGGCCTCTTGGCTATACCTCTTT | 24 |  |
| HLA-DPA1 | DPA1-F1 | 24 | CTCTCTTGACCACGCTGGTACCTA | 40 | 9,660 |
|  | DPA1-R1 | 25 | TTGGCCTCTTGGCTATACCTCTTTT | 41 |  |
| HLA-DPB1 | DPB1-F1 | 24 | ATTGAAGACAAGGAATCGAAGTCC | 25 | 12,444 |
|  | DPB1-R1 | 24 | TCCCCCGATGGAAGATATTATTTG | 26 |  |
| HLA-DPB1 | DPB1_pro-F2 | 24 | CCTCCTGACCCTGATGACAGTCCT | 42 | 5,898 |
|  | DPB1_pro-R2 | 24 | CCATCTGCCCCTCAAGCACCTCAA | 43 |  |
|  | DPB1-F2 | 26 | CTCAGTGCTCGCCCCTCCCTAGTGAT | 44 | 7,220 |
|  | DPB1-R2 | 26 | GCACAGTAGCTTTCGGGAATTGACCA | 45 |  |
| HLA-DQA1 | DQA1-F1 | 21 | GCAAAGGTATTGCTTGGGCTA | 27 | 7,384 |
|  | DQA1-R1 | 21 | CAGACTGCGCCTCTATTCAGG | 28 |  |

TABLE 4 -continued

| HLA-class II gene | Name of primer | Length of primer (mer) | Primer sequence (5'-3') | Sequence ID No. | Estimated length of PCR product (bp) |
|---|---|---|---|---|---|
| HLA-DQA1 | DQA1-F2 | 20 | GCCAGGGAGGGAAATCAACT | 46 | 7,460 |
|  | DQA1-R2 | 21 | ATCCAGTGGAGGACACAGCAC | 47 |  |
| HLA-DQB1 | DQB1-F3.1 | 24 | AAGAAACAAACTGCCCCTTACACC | 29 | 9,093 |
|  | DQB1-R3.1 | 26 | TAGTATTGCCCCTAGTCACTGTCAAG | 30 |  |
|  | DQB1-F3.1 | 24 | AAGAAACAAACTGCCCCTTACACC | 29 |  |
|  | DQB1-F3.2 | 24 | AAGAAACAAACTGCCCCTTATACC | 48 |  |
| HLA-DQB1 | DQB1-R3.1 | 26 | TAGTATTGCCCCTAGTCACTGTCAAG | 30 | 9,093 |
|  | DQB1-R3.2 | 26 | TAGTACTGCCCCTAGTCACTGCCAAG | 49 |  |
|  | DQB1-R3.3 | 26 | TAGTACTGTCCCTAGTCACTGCCAAG | 50 |  |

These primers can be prepared by a method routinely used in this field. Furthermore, the sets of primers described in Table 1 and Table 2 are the most preferable examples. In the method of the present invention, any set of primers can be used as long as the set of primers is a set of a forward primer and a reverse primer capable of annealing to the positions, which correspond to the upstream and downstream of all regions of each HLA gene and sandwich the all regions.

(2) Step of PCR Amplification

In the method of the present invention, a test sample (DNA) is amplified by PCR using the sets of primers prepared in the above step (1).

The PCR amplification reaction is performed in accordance with a general protocol and more specifically, as follows.

1. DNA is extracted from a test sample depending upon the form of the sample.
2. The DNA extracted is quantified and the concentrations of primers are appropriately set to prepare the reaction solution.
3. Reaction conditions are set and a PCR is performed. For example:
Thermal denaturation step (usually 92 to 97° C.)
Annealing step (usually 55 to 72° C.)
Extension step (usually 65 to 80° C.)

In the method of the present invention, in the case of a HLA gene (except HLA-DRB1), the temperature of the annealing step is preferably set at about 60° C. Owing to the annealing at about 60° C., alleles can be produced at the equivalent ratio (uniformly). In the case of a HLA-DRB1, the temperature of the annealing step is preferably set at about 70° C. Owing to the annealing at about 70° C., a desired DR subtype alone can be specifically produced.

4. The obtained PCR product is purified and subjected to the following nucleotide sequencing step.

(3) Step of Nucleotide Sequencing

Next, the nucleotide sequence of the PCR product (amplified DNA) produced in the above step (2) is determined. The step is preferably performed by a technique called next-generation sequencing (or ultrahigh sequencing). With respect to the next-generation sequencing, see, for example, "Experimental Medicine", Vol. 27, No. 1, 2009 (Yodo-sha).

The sequence herein is determined by a method based on pyro-sequencing, which is employed in a genome sequencer FLX system of Roche. The sequencing method will be described below.

1. The PCR product obtained in the above step (2) is broken up by a nebulizer into fragments of about 500 bases.
2. To an end of each of the DNA fragments, a DNA adaptor is attached.
3. DNA fragments attached with a DNA adaptor are dissociated into single stranded DNA fragments, which are allowed to bind to beads via the adaptor. The obtained beads are encompassed and taken in a water-in-oil emulsion (a micro-reactor environment containing a single DNA fragment bound to a single bead is formed).
4. Emulsion PCR is performed to form copies of each DNA fragment on a bead (Each DNA fragment is clonally amplified in each micro reactor. In this manner, many fragments can be simultaneously and in parallel amplified without competition with other sequences). Subsequently, the emulsion is destroyed and beads having amplified DNA fragments are collected.
5. The beads are concentrated and loaded in a pico-titer plate (a single well has a size enough to place a single bead).
6. Pyrophosphoric acid produced by a polymerase during an enzymatic reaction is detected with respect to each bead by a fluorescent reaction of luciferase. Based on the intensity and the pattern of fluorescence thus emitted, the nucleotide sequence of DNA is determined. Four types of nucleic acids (A, C, G, T) are added in a predetermined order. The chemiluminescence pattern in accordance with the nucleic acid added is recorded. Based on the intensity of signal and positional data in combination, the nucleotide sequence is determined.

(4) Step of DNA Typing

Subsequently, the nucleotide sequence obtained in step (3) is compared with data of known HLA alleles within the nucleotide sequencing database. In this manner, the allele type (up to 8 digits) contained in the test sample is determined.

In the method of the present invention, typical sets of primers are listed in Table 1 (described above). The method of the present invention is characterized in that primers are designed so as to correspond to all regions of each of the genes of HLA class I and HLA class II except HLA-DRB1 and the positions sandwiching exon 2 to 3' untranslated region of HLA-DRB1 and the sequence of the DNA amplified so as to correspond to almost all regions is determined. In this manner, phase ambiguity (uncertainty) is eliminated and information on a null allele can be obtained.

EXAMPLES

The present invention will be more specifically described by way of Examples below; however, the present invention is not limited to these Examples.

Example 1

Experimental Method

Figure 4:
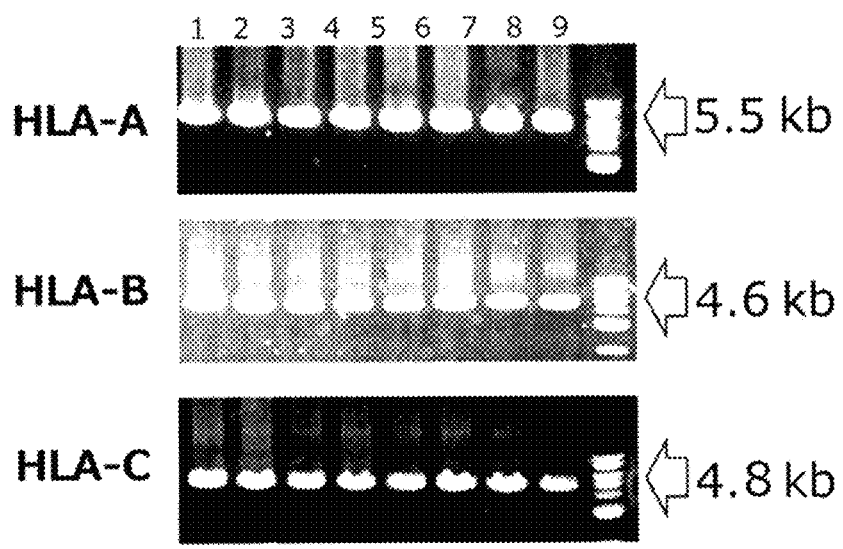
FIG. 4 An agarose gel electrophoretic pattern showing amplification states of PCR products amplified in Example 1.
Figure 5:
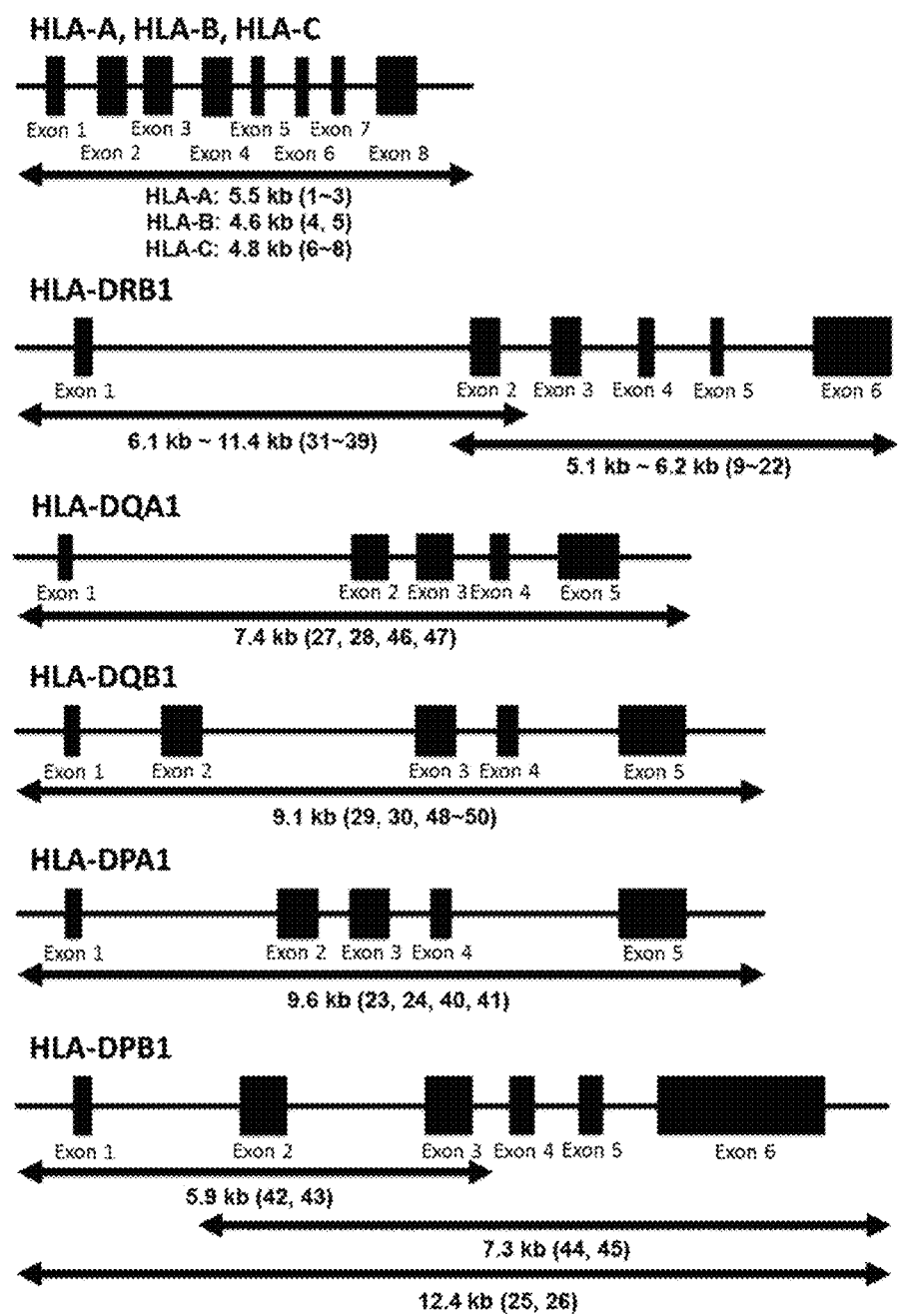
FIG. 5 A diagram schematically showing the structure of a HLA gene and the position to which a PCR primer is designed to bind (SEQ ID No. of the primer designed in the indicated region is indicated within parentheses).

1. Using genomic DNA already extracted as a template and primer sets specific to individual HLA class I genes (see Table 1: SEQ ID Nos. 1 to 8), a PCR was carried out. The procedure is more specifically as follows.
(1) PCR amplification was performed by use of Prime STAR GXL polymerase (TaKaRa). More specifically, to 50 ng of a genomic DNA solution, 4 μL of 5× PrimeSTAR GXL buffer, 1.6 μL of a dNTP solution, PCR primers (4 μL (1 pmol/μL) for each) and 0.8 μL of Prime STAR GXL polymerase were added. The whole amount of the reaction solution was adjusted to be 20 μL with sterilized water.
(2) After kept at 94° C. for 2 minutes, the reaction solution was subjected to a step consisting of a reaction at 98° C. for 10 seconds, a reaction at 60° C. for 20 seconds and a reaction at 68° C. for 5 minutes. This step was repeated 30 times. Note that, for the PCR amplification, Gene Amp PCR System 9700 (Applied Biosystems) was used. After the PCR, the amplification states of PCR products were checked by agarose gel electrophoresis. The electrophoretic patterns were shown in FIG. 4.
2. The nucleotide sequences of the PCR products were determined specifically as follows.
(1) A PCR product was purified by QIAquick PCR Purification Kit (QIAGEN) in accordance with the standard protocol.
(2) The concentration of the purified PCR product was measured by PicoGreen dsDNA Quantitation Kit (Invitrogen) in accordance with the standard protocol.
(3) A solution of the purified PCR product, a concentration of which was adjusted to be 500 ng/100 μL, was subjected to construction of a rapid library, and then, emulsion PCR and sequencing by Genome Sequencer (GS) Junior (Roche) were carried out in accordance with the standard protocol to obtain nucleotide sequences of 10,000 reads per sample.
(4) These sequences were connected and edited by GS de novo Assembler (Roche). Thereafter, a search for homology with known nucleotide sequences on a DNA database was performed to identify alleles on the HLA gene.
[Discussion]
In HLA-A, HLA-B and HLA-C, PCR primers, which specifically amplify 5.5 kb, 4.6 kb and 4.8 kb, respectively, were designed. PCR conditions were studied and agarose gel electrophoresis of the resultant PCR products was performed. As a result, it was found that HLA class I genes all provide a single PCR amplified product at a position corresponding to a desired molecular weight (FIG. 4). Furthermore, the nucleotide sequences of the PCR products were determined by the Sanger method. As a result, HLA alleles were obtained in consistent with known documents. From this, it was confirmed that the PCR system of the invention can be used for HLA typing.

Using three specimens of a HLA-B*40:02 homozygote and 17 specimens of a HLA-B*40:02 heterozygote including combinations of alleles (B*40 and B*55), in which phase ambiguity was observed in a conventional DNA typing method, a PCR was performed. As the result of HLA typing of the PCR products derived from the HLA-B gene by GS Junior, HLA-B*40:02:01:01 was detected from all specimens. In the 17 heterozygote specimens, 2 types of novel alleles were detected in addition to 15 alleles already known. In particular, with respect to a single specimen having a combination of alleles (B*40 and B*55) in which phase ambiguity was observed, HLA-B*40:02:01:01 and HLA-B*55:02:01:01 were identified by typing. From this, it was demonstrated that the method of the invention enables HLA typing at a 8-digit level without phase ambiguity; and that the method of the invention is an excellent tool for efficiently detecting a substitution, an insertion and a deletion of bases in a promoter and introns, which are causes of a null allele.

Example 2

Experimental Method

1. Using a genomic DNA already extracted as a template and primer sets specific to individual HLA class I and HLA class II genes (see Tables 1 to 4: SEQ ID Nos. 1 to 8, 9 to 22, 31 to 50), a PCR was carried out. The procedure is more specifically as follows.
(1) PCR amplification was performed by use of Prime STAR GXL polymerase (TaKaRa). More specifically, to 50 ng of a genomic DNA solution, 4 μL of 5× PrimeSTAR GXL buffer, 1.6 μL of a dNTP solution, PCR primers (1 to 7 μL (4 pmol/μL)) and 0.8 μL of Prime STAR GXL polymerase were added. The whole amount of the reaction solution was adjusted to be 20 μL with sterilized water.
(2) After kept at 94° C. for 2 minutes, the reaction solution was subjected to a step consisting of a reaction at 98° C. for 10 seconds and a reaction at 70° C. for 5 minutes. This step was repeated 30 times. Note that, for the PCR amplification, Gene Amp PCR System 9700 (Applied Biosystems) was used. After the PCR, the amplification states of PCR products were checked by agarose gel electrophoresis. The electrophoretic patterns were shown in FIG. 6.
2. The nucleotide sequences of the PCR products were determined specifically as follows.
(1) A PCR product was purified by QIAquick PCR Purification Kit (QIAGEN) in accordance with the standard protocol.
(2) The concentration of the purified PCR product was measured by PicoGreen dsDNA Quantitation Kit (Invitrogen) in accordance with the standard protocol.
(3) The purified PCR product, the concentration of which was adjusted to be 100 ng, was subjected to construction of a fragment library, and then emulsion PCR and sequencing by Ion Personal Genome Machine (Ion PGM) (Life Technologies) were carried out in accordance with the standard protocol to obtain nucleotide sequences of 300,000 reads per sample.
(4) These sequences were connected and edited by GS De Novo Assembler (Roche). Thereafter, a search for homology with known nucleotide sequences on a DNA database was performed to identify alleles on the HLA gene.

[Results and Discussion]

Figure 6:
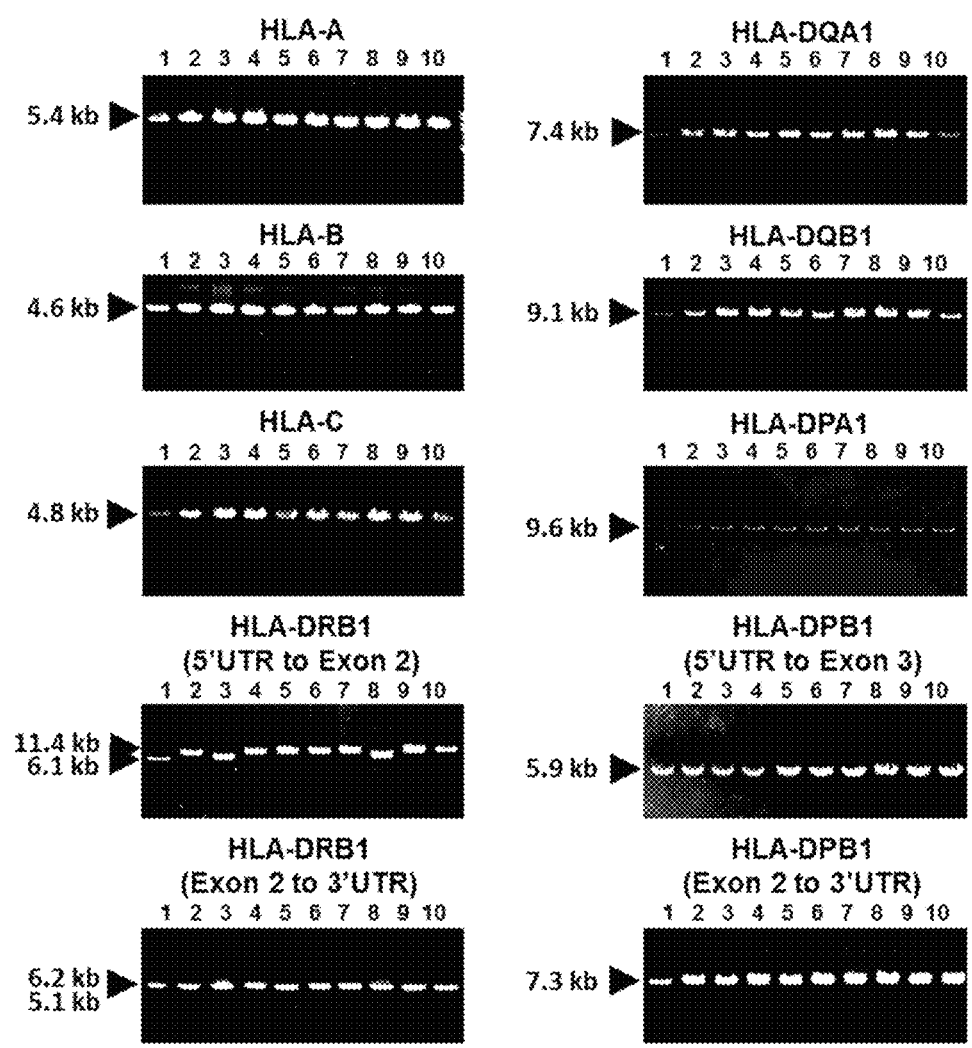
FIG. 6 An agarose gel electrophoretic pattern showing the amplification states of amplified PCR products of a HLA gene in Example 2.

1. PCR primers, which specifically amplify 4 kb to 12 kb in the region from a 5' untranslated region to exon 2 of HLA-A, HLA-B, HLA-C and HLA-DRB1, the region from exon 2 to a 3' untranslated region of HLA-DRB1, the region from a 5' untranslated region to exon 2 of HLA-DQB1 and HLA-DPB1 and the region from exon 2 to a 3' untranslated region of HLA-DPB1, were designed. PCR conditions were studied and agarose gel electrophoresis of the resultant PCR products was performed. As a result, it was found that HLA class I and HLA class II genes all provide a single amplified product at a position corresponding to a desired molecular weight (FIG. 6). Furthermore, the nucleotide sequences of the PCR products were determined by the Sanger method. As a result, HLA alleles were obtained in consistent with known documents. It was confirmed herein again that the PCR system of the invention can be used for HLA typing.

2. Using four specimens containing a combination of alleles, in which phase ambiguity is observed in a conventional DNA typing method, a PCR was performed. PCR products derived from the regions from a 5' untranslated region to exon 2 of HLA-A, HLA-B, HLA-C and HLA-DRB1 genes, the region from exon 2 to a 3' untranslated region of a HLA-DRB1 gene, the region from a 5' untranslated region to exon 2 of HLA-DQB1 and HLA-DPB1 genes, and the region from exon 2 to a 3' untranslated region of a HLA-DPB1 gene were subjected to HLA typing by Ion PGM. As a result, typing of whole gene regions of HLA-A, HLA-B, HLA-C, HLA-DRB1 and HLA-DQB1 were successfully made. With respect to HLA-DPB1, typing of an exon alone was successfully made. Furthermore, in each of the HLA-B, HLA-C, HLA-DRB1 and HLA-DQB1 genes, a novel allele was detected. From this, it was demonstrated that the method of the invention enables HLA typing at a 8-digit level without phase ambiguity; and that the method of the invention is an excellent tool for efficiently detecting a substitution, an insertion and a deletion of bases in a promoter and introns, which are causes of a null allele.

Example 3

Experimental Method

1. Genomic DNA was extracted by using Buccal Cell DNA Extraction Kit, BuccalQuick (TRIMGEN).

2. The genomic DNA extracted by use of Buccal Cell DNA Extraction Kit, BuccalQuick (TRIMGEN) was further purified with isopropanol and ethanol.

3. Using a QIAamp DNA Blood Mini Kit (QIAGEN), genomic DNA was extracted.

4. Three each of genomic DNA specimens extracted in items 1 to 3 above were subjected to PCR using primer sets specific to HLA-A, HLA-B, HLA-C and HLA-DQB1 performed in the same experimental method as in Example 1 and Example 2 (see Table 1 and Table 4: SEQ ID Nos. 1 to 8, 29, 30, 48 to 50). After the PCR, the amplification states of the PCR products were checked by agarose gel electrophoresis. The electrophoretic patterns were shown in FIG. 7.

[Experimental Results and Discussion]

Figure 7:
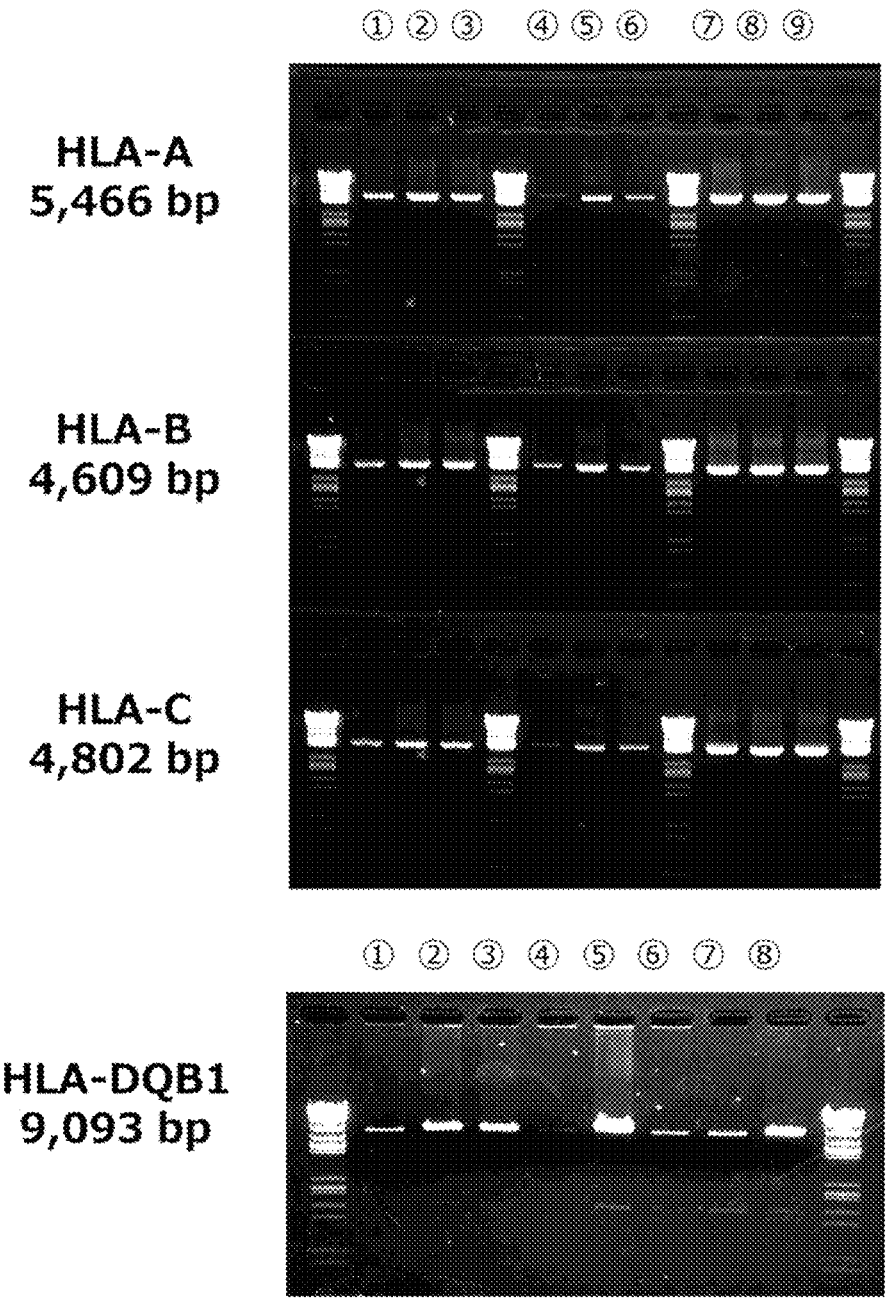
FIG. 7 An agarose gel electrophoretic pattern of amplified PCR products obtained by three types of DNA extraction methods in Example 3.

In FIG. 7, lanes 1 to 3 show the amplification states of PCR products in the case where extraction was made by Experimental method 1, lanes 4 to 6 show the amplification states of PCR products in the case where extraction was made by Experimental method 2, and lanes 7 to 9 show the amplification state of PCR products in the case where extraction was made by Experimental method 3. PCR amplification in the case where genomic DNA extracted by Experimental method 1 was used as a template in any gene is equivalent to PCR amplification in the case where genomic DNA extracted by Experimental method 3 was used, and a desired PCR product was obtained. In Experimental method 3, blood must be taken; however in Experimental method 1, cells can be taken from the oral mucous membrane. Therefore, it was demonstrated that if the method of the present invention is employed, HLA typing can be sufficiently performed even if blood cannot be taken.

REFERENCE TO A SEQUENCE LISTING, A TABLE, OR A COMPUTER PROGRAM LISTING APPENDIX SUBMITTED AS AN ASCII TEXT FILE

The material in the ASCII text file, named WING2-52072-seql.text, created Apr. 1, 2016, file size 12,288 bytes, is hereby incorporated by reference.

The invention claimed is:

1. A method for DNA typing of HLA, comprising the following steps:
   (1) a step of preparing a set of primers comprising:
   (a) at least one primer subset selected from the group consisting of:
      (a1) an (a1) primer subset that can amplify from an enhancer-promoter to a 3'UTR region of HLA-A gene, the (a1) primer subset comprising an (a1) forward primer and an (a1) reverse primer, the (a1) forward primer comprising SEQ ID No. 1 or 2, and the (a1) reverse primer comprising SEQ ID No. 3;
      (a2) an (a2) primer subset that can amplify from an enhancer-promoter to a 3'UTR region of HLA-B gene, the (a2) primer subset comprising an (a2) forward primer and an (a2) reverse primer, the (a2) forward primer comprising SEQ ID No. 4, and the (a2) reverse primer comprising SEQ ID No. 5;
      (a3) an (a3) primer subset that can amplify from an enhancer-promoter to a 3'UTR region of HLA-C gene, the (a3) primer subset comprising an (a3) forward primer and an (a3) reverse primer, the (a3) forward primer comprising SEQ ID No. 6 or 7, and the (a3) reverse primer comprising SEQ ID No. 8;
      (a4) an (a4) primer subset that can amplify from an enhancer-promoter to a 3'UTR region of HLA-DQA1 gene, the (a4) primer subset comprising an (a4) forward primer and an (a4) reverse primer, the (a4) forward primer comprising SEQ ID No. 27 or 46, and the (a4) reverse primer comprising SEQ ID No. 28 or 47;
      (a5) an (a5) primer subset that can amplify from an enhancer-promoter to a 3'UTR region of HLA-DQB1 gene, the (a5) primer subset comprising an (a5) forward primer and an (a5) reverse primer, the (a5) forward primer comprising SEQ ID No. 29 or 48, and the (a5) reverse primer comprising SEQ ID No. 30, 49, or 50;
      (a6) an (a6) primer subset that can amplify from an enhancer-promoter to a 3'UTR region of HLA-DPA1 gene, the (a6) primer subset comprising an (a6) forward primer and an (a6) reverse primer, the (a6) forward primer comprising SEQ ID No. 23 or 40, and the (a6) reverse primer comprising SEQ ID No. 24 or 41; and
      (a7) an (a7) primer subset that can amplify from an intron or an enhancer-promoter to a 3'UTR region of HLA-DPB1 gene, the (a7) primer subset comprising an (a7) forward primer and an (a7) reverse primer, the (a7) forward primer comprising SEQ ID No. 25, 42, or 44, and the (a7) reverse primer comprising SEQ ID No. 26, 43, or 45; and
   (b) a (b) primer subset that can amplify from exon 2 to a 3'UTR region of HLA-DRB1 gene;
   wherein, the (b) primer subset comprises:
   (i) a (b1) forward primer comprising SEQ ID No. 9, 10 or 31 and a (b1) reverse primer comprising SEQ ID No. 11 or 32;
   (ii) a (b2) forward primer comprising SEQ ID No. 12 or 31 and a (b2) reverse primer comprising SEQ ID No. 11 or 33;
   (iii) a (b3) forward primer comprising SEQ ID No. 13 or 34 and a (b3) reverse primer comprising SEQ ID No. 14 or 32;
   (iv) a (b4) forward primer comprising SEQ ID No. 15 or 31 and a 04) reverse primer comprising SEQ ID No. 16 or 32;
   (v) a (b5) forward primer comprising SEQ ID No. 13 or 31 and a (b5) reverse primer comprising SEQ ID No. 14, 35 or 36;
   (vi) a (b6) forward primer comprising SEQ ID No. 13 or 31 and a (b6) reverse primer comprising SEQ ID No. 14, 32 or 37;
   (vii) a (b7) forward primer comprising SEQ ID No. 17 or 38 and a (b7) reverse primer comprising SEQ ID No. 18 or 36;
   (viii) a (b8) forward primer comprising SEQ ID No. 13 or 31 and a (b8) reverse primer comprising SEQ ID No. 14 or 39;
   (ix) a (b9) forward primer comprising SEQ ID No. 19 or 38 and a (b9) reverse primer comprising SEQ ID No. 20 or 36; and
   (x) a (b10) forward primer comprising SEQ ID No. 21 or 31 and a (b10) reverse primer comprising SEQ ID No. 22 or 32;
   (2) a step of amplifying a test sample (DNA) by a PCR using the set of primers;
   (3) a step of determining the nucleotide sequences of PCR amplified products; and (4) a step of optionally carrying out a homology search within a database.

2. A method for DNA typing of HLA, comprising the following steps:

(1) a step of preparing a set of primers comprising:

(a1) an (a1) primer subset that can amplify from an enhancer-promoter to a 3'UTR region of HLA-A gene, the (a1) primer subset comprising an (a1) forward primer and an (a1) reverse primer, the (a1) forward primer comprising SEQ ID No. 1 or 2, and the (a1) reverse primer comprising SEQ ID No. 3;

(a2) an (a2) primer subset that can amplify from an enhancer-promoter to a 3'UTR region of HLA-B gene, the (a2) primer subset comprising an (a2) forward primer and an (a2) reverse primer, the (a2) forward primer comprising SEQ ID No. 4, and the (a2) reverse primer comprising SEQ ID No. 5;

(a3) an (a3) primer subset that can amplify from an enhancer-promoter to a 3'UTR region of HLA-C gene, the (a3) primer subset comprising an (a3) forward primer and an (a3) reverse primer, the (a3) forward primer comprising SEQ ID No. 6 or 7, and the (a3) reverse primer comprising SEQ ID No. 8;

(a4) an (a4) primer subset that can amplify from an enhancer-promoter to a 3'UTR region of HLA-DQA1 gene, the (a4) primer subset comprising an (a4) forward primer and an (a4) reverse primer, the (a4) forward primer comprising SEQ ID No. 27 or 46, and the (a4) reverse primer comprising SEQ ID No. 28 or 47;

(a5) an (a5) primer subset that can amplify from an enhancer-promoter to a 3'UTR region of HLA-DQB1 gene, the (a5) primer subset comprising an (a5) forward primer and an (a5) reverse primer, the (a5) forward primer comprising SEQ ID No. 29 or 48, and the (a5) reverse primer comprising SEQ ID No. 30, 49, or 50;

(a6) an (a6) primer subset that can amplify from an enhancer-promoter to a 3'UTR region of HLA-DPA1 gene, the (a6) primer subset comprising an (a6) forward primer and an (a6) reverse primer, the (a6) forward primer comprising SEQ ID No. 23 or 40, and the (a6) reverse primer comprising SEQ ID No. 24 or 41; and (a7) an (a7) primer subset that can amplify from an intron or an enhancer-promoter to a 3'UTR region of HLA-DPB1 gene, the (a7) primer subset comprising an (a7) forward primer and an (a7) reverse primer, the (a7) forward primer comprising SEQ ID No. 25, 42, or 44, and the (a7) reverse primer comprising SEQ ID No. 26, 43, or 45; and (b) a (b) primer subset that can amplify from exon 2 to a 3'UTR region of HLA-DRB1 gene;

wherein, the (b), primer subset comprises:

(i) a (b1) forward primer comprising SEQ ID No. 9, 10 or 31 and a (b1) reverse primer comprising SEQ ID No. 11 or 32;

(ii) a (b2) forward primer comprising SEQ ID No. 12 or 31 and a (b2) reverse primer comprising SEQ ID No. 11 or 33;

(iii) a (b3) forward primer comprising SEQ ID No. 13 or 34 and a (b3) reverse primer comprising SEQ ID No. 14 or 32;

(iv) a (b4) forward primer comprising SEQ ID No. 15 or 31 and a (b4) reverse primer comprising SEQ ID No. 16 or 32;

(v) a (b5) forward primer comprising SEQ ID No. 13 or 31 and a (b5) reverse primer comprising SEQ ID No. 14, 35 or 36;

(vi) a (b6) forward primer comprising SEQ ID No. 13 or 31 and a (b6) reverse primer comprising SEQ ID No. 14, 32 or 37;

(vii) a (b7) forward primer comprising SEQ ID No. 17 or 38 and a (b7) reverse primer comprising SEQ ID No. 18 or 36;

(viii) a (b8) forward primer comprising SEQ ID No. 13 or 31 and a (b8) reverse primer comprising SEQ ID No. 14 or 39;

(ix) a (b9) forward primer comprising SEQ ID No. 19 or 38 and a (b9) reverse primer comprising SEQ ID No. 20 or 36; and (x) a (b10) forward primer comprising SEQ ID No. 21 or 31 and a (b10) reverse primer comprising SEQ ID No. 22 or 32;

(2) a step of amplifying a test sample (DNA) by a PCR using the set of primers;

(3) a step of determining the nucleotide sequences of PCR amplified products; and (4) a step of optionally carrying out a homology search within a database.

3. The method according to claim 1, wherein the (a1) forward primer consists of SEQ ID No. 1 or 2, and the (a1) reverse primer consists of SEQ ID No. 3.

4. The method according to claim 1, wherein the (a2) forward primer consists of SEQ ID No. 4, and the (a2) reverse primer consists of SEQ ID No. 5.

5. The method according to claim 1, wherein the (a3) forward primer consists of SEQ ID No. 6 or 7, and the (a3) reverse primer consists of SEQ ID No. 8.

6. The method according to claim 1, wherein the (a4) forward primer consists of SEQ ID No. 27 or 46, and the (a4) reverse primer consists of SEQ ID No. 28 or 47.

7. The method according to claim 1, wherein the (a5) forward primer consists of SEQ ID No. 29 or 48, and the (a5) reverse primer consists of SEQ ID No. 30, 49 or 50.

8. The method according to claim 1, wherein the (a6) forward primer consists of SEQ ID No. 23 or 40, and the (a6) reverse primer consists of SEQ ID No. 24 or 41.

9. The method according to claim 1, wherein the (a7) forward primer consists of SEQ ID No. 25, 42 or 44, and the (a7) reverse primer consists of SEQ ID No. 26, 43 or 45.

10. The method according to claim 2, wherein the (a1) forward primer consists of SEQ ID No. 1 or 2, and the (a1) reverse primer consists of SEQ ID No. 3.

11. The method according to claim 2, wherein the (a2) forward primer consists of SEQ ID No. 4, and the (a2) reverse primer consists of SEQ ID No. 5.

12. The method according to claim 2, wherein the (a3) forward primer consists of SEQ ID No. 6 or 7, and the (a3) reverse primer consists of SEQ ID No. 8.

13. The method according to claim 2, wherein the (a4) forward primer consists of SEQ ID No. 27 or 46, and the (a4) reverse primer consists of SEQ ID No. 28 or 47.

14. The method according to claim 2, wherein the (a5) forward primer consists of SEQ ID No. 29 or 48, and the (a5) reverse primer consists of SEQ ID No. 30, 49 or 50.

15. The method according to claim 2, wherein the (a6) forward primer consists of SEQ ID No. 23 or 40, and the (a6) reverse primer consists of SEQ ID No. 24 or 41.

16. The method according to claim 2, wherein the (a7) forward primer consists of SEQ ID No. 25, 42 or 44, and the (a7) reverse primer consists of SEQ ID No. 26, 43 or 45.

17. The method according to claim 1, wherein:

(i) the (b1) forward primer consists of SEQ ID No. 9, 10 or 31 and the (b1) reverse primer consists of SEQ ID No. 11 or 32;

(ii) the (b2) forward primer consists of SEQ ID No. 12 or 31 and the (b2) reverse primer consists of SEQ ID No. 11 or 33;
(iii) the (b3) forward primer consists of SEQ ID No. 13 or 34 and the (b3) reverse primer consists of SEQ ID No. 14 or 32;
(iv) the (b4) forward primer consists of SEQ ID No. 15 or 31 and the (b4) reverse primer consists of SEQ ID No. 16 or 32;
(v) the (b5) forward primer consists of SEQ ID No. 13 or 31 and the (b5) reverse primer consists of SEQ ID No. 14, 35 or 36;
(vi) the (b6) forward primer consists of SEQ ID No. 13 or 31 and the (b6) reverse primer consists of SEQ ID No. 14, 32 or 37;
(vii) the (b7) forward primer consists of SEQ ID No. 17 or 38 and the (b7) reverse primer consists of SEQ ID No. 18 or 36;
(viii) the (b8) forward primer consists of SEQ ID No. 13 or 31 and the (b8) reverse primer consists of SEQ ID No. 14 or 39;
(ix) the (b9) forward primer consists of SEQ ID No. 19 or 38 and the (b9) reverse primer consists of SEQ ID No. 20 or 36; and
(x) the (b10) forward primer consists of SEQ ID No. 21 or 31 and the (b10) reverse primer consists of SEQ ID No. 22 or 32.

18. The method according to claim 2, wherein
(i) the (b1) forward primer consists of SEQ ID No. 9, 10 or 31 and the (b1) reverse primer consists of SEQ ID No. 11 or 32;
(ii) the (b2) forward primer consists of SEQ ID No. 12 or 31 and the (b2) reverse primer consists of SEQ ID No. 11 or 33;
(iii) the (b3) forward primer consists of SEQ ID No. 13 or 34 and the (b3) reverse primer consists of SEQ ID No. 14 or 32;
(iv) the (b4) forward primer consists of SEQ ID No. 15 or 31 and the (b4) reverse primer consists of SEQ ID No. 16 or 32;
(v) the (b5) forward primer consists of SEQ ID No. 13 or 31 and the (b5) reverse primer consists of SEQ ID No. 14, 35 or 36;
(vi) the (b6) forward primer consists of SEQ ID No. 13 or 31 and the (b6) reverse primer consists of SEQ ID No. 14, 32 or 37;
(vii) the (b7) forward primer consists of SEQ ID No. 17 or 38 and the (b7) reverse primer consists of SEQ ID No. 18 or 36;
(viii) the (b8) forward primer consists of SEQ ID No. 13 or 31 and the (b8) reverse primer consists of SEQ ID No. 14 or 39;
(ix) the (b9) forward primer consists of SEQ ID No. 19 or 38 and the (b9) reverse primer consists of SEQ ID No. 20 or 36; and
(x) the (b10) forward primer consists of SEQ ID No. 21 or 31 and the (b10) reverse primer consists of SEQ ID No. 22 or 32.

\* \* \* \* \*

```
SEQUENCE LISTING

<160> NUMBER OF SEQ ID NOS: 50

<210> SEQ ID NO 1
<211> LENGTH: 28
<212> TYPE: DNA
<213> ORGANISM: Artificial Sequence
<220> FEATURE:
<223> OTHER INFORMATION: Synthesized Polynucleotide

<400> SEQUENCE: 1
aactcagagc taaggaatga tggcaaat                                       28

<210> SEQ ID NO 2
<211> LENGTH: 28
<212> TYPE: DNA
<213> ORGANISM: Artificial Sequence
<220> FEATURE:
<223> OTHER INFORMATION: Synthesized Polynucleotide

<400> SEQUENCE: 2
aactcagagc tatggaatga tggtaaat                                       28
```

<210> SEQ ID NO 3
<211> LENGTH: 28
<212> TYPE: DNA
<213> ORGANISM: Artificial Sequence
<220> FEATURE:
<223> OTHER INFORMATION: Synthesized Polynucleotide

<400> SEQUENCE: 3
atataaccat catcgtgtcc caaggttc                                28

<210> SEQ ID NO 4
<211> LENGTH: 25
<212> TYPE: DNA
<213> ORGANISM: Artificial Sequence
<220> FEATURE:
<223> OTHER INFORMATION: Synthesized Polynucleotide

<400> SEQUENCE: 4
cccggttgca atagacagta acaaa                                   25

<210> SEQ ID NO 5
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 5
gggtccaatt tcacagacaa atgt                                    24

<210> SEQ ID NO 6
<211> LENGTH: 25
<212> TYPE: DNA
<213> ORGANISM: Artificial Sequence
<220> FEATURE:
<223> OTHER INFORMATION: Synthesized Polynucleotide

<400> SEQUENCE: 6
tgcttagatg tgcatagttc acgaa                                   25

<210> SEQ ID NO 7
<211> LENGTH: 25
<212> TYPE: DNA
<213> ORGANISM: Artificial Sequence
<220> FEATURE:
<223> OTHER INFORMATION: Synthesized Polynucleotide

<400> SEQUENCE: 7
tgcttagatg tgcatagttc cggaa                                   25

<210> SEQ ID NO 8
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 8
tggacccaat tttacaaaca aata                                    24

<210> SEQ ID NO 9
<211> LENGTH: 26
<212> TYPE: DNA
<213> ORGANISM: Artificial Sequence
<220> FEATURE:

<223> OTHER INFORMATION: Synthesized Polynucleotide

<400> SEQUENCE: 9
gcacgtttct tgtggcagct taagtt                                              26

<210> SEQ ID NO 10
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 10
gcacgtttct tgtggcagct aaagtt                                              26

<210> SEQ ID NO 11
<211> LENGTH: 21
<212> TYPE: DNA
<213> ORGANISM: Artificial Sequence
<220> FEATURE:
<223> OTHER INFORMATION: Synthesized Polynucleotide

<400> SEQUENCE: 11
atgcacggga ggccatacgg t                                                   21

<210> SEQ ID NO 12
<211> LENGTH: 22
<212> TYPE: DNA
<213> ORGANISM: Artificial Sequence
<220> FEATURE:
<223> OTHER INFORMATION: Synthesized Polynucleotide

<400> SEQUENCE: 12
tttcctgtgg cagcctaaga gg                                                  22

<210> SEQ ID NO 13
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 13
cacagcacgt ttcttggagt actc                                                24

<210> SEQ ID NO 14
<211> LENGTH: 21
<212> TYPE: DNA
<213> ORGANISM: Artificial Sequence
<220> FEATURE:
<223> OTHER INFORMATION: Synthesized Polynucleotide

<400> SEQUENCE: 14
atgcacagga ggccataggg t                                                   21

<210> SEQ ID NO 15
<211> LENGTH: 27
<212> TYPE: DNA
<213> ORGANISM: Artificial Sequence
<220> FEATURE:
<223> OTHER INFORMATION: Synthesized Polynucleotide

<400> SEQUENCE: 15
agcacgtttc ttggagcagg ttaaaca                                             27

<210> SEQ ID NO 16
<211> LENGTH: 21
<212> TYPE: DNA
<213> ORGANISM: Artificial Sequence
<220> FEATURE:
<223> OTHER INFORMATION: Synthesized Polynucleotide

<400> SEQUENCE: 16
atgcatggga ggcaggaagc a                                      21

<210> SEQ ID NO 17
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 17
cacagcacgt ttcctgtggc aggg                                   24

<210> SEQ ID NO 18
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 18
cagatgcatg ggaggcagga agcg                                   24

<210> SEQ ID NO 19
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 19
cacagcacgt ttcttgaagc agga                                   24

<210> SEQ ID NO 20
<211> LENGTH: 21
<212> TYPE: DNA
<213> ORGANISM: Artificial Sequence
<220> FEATURE:
<223> OTHER INFORMATION: Synthesized Polynucleotide

<400> SEQUENCE: 20
atgcatggga ggcaggaagc g                                      21

<210> SEQ ID NO 21
<211> LENGTH: 23
<212> TYPE: DNA
<213> ORGANISM: Artificial Sequence
<220> FEATURE:
<223> OTHER INFORMATION: Synthesized Polynucleotide

<400> SEQUENCE: 21
acagcacgtt tcttggagga ggt                                    23

<210> SEQ ID NO 22
<211> LENGTH: 33
<212> TYPE: DNA
<213> ORGANISM: Artificial Sequence
<220> FEATURE:
<223> OTHER INFORMATION: Synthesized Polynucleotide

<400> SEQUENCE: 22
tggaatgtct aaagcaagct atttaacata tgt                                    33

<210> SEQ ID NO 23
<211> LENGTH: 25
<212> TYPE: DNA
<213> ORGANISM: Artificial Sequence
<220> FEATURE:
<223> OTHER INFORMATION: Synthesized Polynucleotide

<400> SEQUENCE: 23
tgatttctct gataggtgaa tccca                                             25

<210> SEQ ID NO 24
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 24
ttggcctctt ggctatacct cttt                                              24

<210> SEQ ID NO 25
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 25
attgaagaca aggaatcgaa gtcc                                              24

<210> SEQ ID NO 26
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 26
tcccccgatg gaagatatta tttg                                              24

<210> SEQ ID NO 27
<211> LENGTH: 21
<212> TYPE: DNA
<213> ORGANISM: Artificial Sequence
<220> FEATURE:
<223> OTHER INFORMATION: Synthesized Polynucleotide

<400> SEQUENCE: 27
gcaaaggtat tgcttgggct a                                                 21

<210> SEQ ID NO 28
<211> LENGTH: 21
<212> TYPE: DNA
<213> ORGANISM: Artificial Sequence
<220> FEATURE:
<223> OTHER INFORMATION: Synthesized Polynucleotide

<400> SEQUENCE: 28
cagactgcgc ctctattcag g                                                 21

<210> SEQ ID NO 29
<211> LENGTH: 24

<212> TYPE: DNA
<213> ORGANISM: Artificial Sequence
<220> FEATURE:
<223> OTHER INFORMATION: Synthesized Polynucleotide

<400> SEQUENCE: 29
aagaaacaaa ctgcccctta cacc                                   24

<210> SEQ ID NO 30
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 30
tagtattgcc cctagtcact gtcaag                                 26

<210> SEQ ID NO 31
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 31
ctgctgctcc ttgaggcatc caca                                   24

<210> SEQ ID NO 32
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 32
cttctggctg ttccagtact cggcat                                 26

<210> SEQ ID NO 33
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 33
cttctggctg ttccagtact cagcgt                                 26

<210> SEQ ID NO 34
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 34
ctgctgctcc ctgaggcatc caca                                   24

<210> SEQ ID NO 35
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 35

-continued cttctggctg ttccagtact cctcat                                                                 26

<210> SEQ ID NO 36
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 36
cttctggctg ttccaggact cggcga                                                                 26

<210> SEQ ID NO 37
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 37
cttctggctg ttccagtgct ccgcag                                                                 26

<210> SEQ ID NO 38
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 38
ctgctactcc ttgaggcatc caca                                                                   24

<210> SEQ ID NO 39
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 39
cttctggctg ttccagtact cggcgc                                                                 26

<210> SEQ ID NO 40
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 40
ctctcttgac cacgctggta ccta                                                                   24

<210> SEQ ID NO 41
<211> LENGTH: 25
<212> TYPE: DNA
<213> ORGANISM: Artificial Sequence
<220> FEATURE:
<223> OTHER INFORMATION: Synthesized Polynucleotide

<400> SEQUENCE: 41
ttggcctctt ggctatacct ctttt                                                                  25

<210> SEQ ID NO 42
<211> LENGTH: 24
<212> TYPE: DNA
<213> ORGANISM: Artificial Sequence

```
<220> FEATURE:
<223> OTHER INFORMATION: Synthesized Polynucleotide

<400> SEQUENCE: 42
cctcctgacc ctgatgacag tcct                                          24

<210> SEQ ID NO 43
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 43
ccatctgccc ctcaagcacc tcaa                                          24

<210> SEQ ID NO 44
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 44
ctcagtgctc gcccctccct agtgat                                        26

<210> SEQ ID NO 45
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 45
gcacagtagc tttcgggaat tgacca                                        26

<210> SEQ ID NO 46
<211> LENGTH: 20
<212> TYPE: DNA
<213> ORGANISM: Artificial Sequence
<220> FEATURE:
<223> OTHER INFORMATION: Synthesized Polynucleotide

<400> SEQUENCE: 46
gccagggagg gaaatcaact                                               20

<210> SEQ ID NO 47
<211> LENGTH: 21
<212> TYPE: DNA
<213> ORGANISM: Artificial Sequence
<220> FEATURE:
<223> OTHER INFORMATION: Synthesized Polynucleotide

<400> SEQUENCE: 47
atccagtgga ggacacagca c                                             21

<210> SEQ ID NO 48
<211> LENGTH: 24
<212> TYPE: DNA
<213> ORGANISM: Artificial Sequence
<220> FEATURE:
<223> OTHER INFORMATION: Synthesized Polynucleotide

<400> SEQUENCE: 48
aagaaacaaa ctgcccctta tacc                                          24
```

```
<210> SEQ ID NO 49
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 49
tagtactgcc cctagtcact gccaag                                              26

<210> SEQ ID NO 50
<211> LENGTH: 26
<212> TYPE: DNA
<213> ORGANISM: Artificial Sequence
<220> FEATURE:
<223> OTHER INFORMATION: Synthesized Polynucleotide

<400> SEQUENCE: 50
tagtactgtc cctagtcact gccaag                                              26
```